US012697458B2

(12) United States Patent
Westfall et al.

(10) Patent No.: US 12,697,458 B2
(45) Date of Patent: Aug. 4, 2026

(54) O₂ CONCENTRATOR WITH SIEVE BED BYPASS AND CONTROL METHOD THEREOF

(71) Applicant: Breathe Technologies, Inc., Irvine, CA (US)

(72) Inventors: Tom Westfall, Irvine, CA (US); Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 211 days.

(21) Appl. No.: 18/809,825

(22) Filed: Aug. 20, 2024

(65) Prior Publication Data

US 2024/0408343 A1      Dec. 12, 2024

Related U.S. Application Data

(60) Continuation of application No. 18/109,560, filed on Feb. 14, 2023, now Pat. No. 12,102,767, which is a
(Continued)

(51) Int. Cl.
  *B01D 53/047*       (2006.01)
  *A61M 16/00*       (2006.01)
  (Continued)

(52) U.S. Cl.
  CPC ........ *A61M 16/101* (2014.02); *A61M 16/006* (2014.02); *A61M 16/0063* (2014.02);
  (Continued)

(58) Field of Classification Search
  CPC .............. A61M 16/101; A61M 16/006; A61M 16/0063; A61M 16/20; A61M 2202/0208;
  (Continued)

(56) References Cited

U.S. PATENT DOCUMENTS 4,421,530 A    12/1983  Dalton, Jr. et al.
4,822,384 A     4/1989  Kato et al.
         (Continued)

FOREIGN PATENT DOCUMENTS

CN      102458549 A    5/2012
CN      103180032 A    6/2013
         (Continued)

OTHER PUBLICATIONS

Office Action for Chinese Patent Application No. 202010443845.3; mailed Oct. 25, 2022.
                    (Continued)

*Primary Examiner* — Frank M Lawrence, Jr.
(74) *Attorney, Agent, or Firm* — Stetina Garred Brucker & Newboles

(57) ABSTRACT

An oxygen concentrator includes one or more adsorbent sieve beds operable to remove nitrogen from air to produce concentrated oxygen gas at respective outlets thereof, a product tank fluidly coupled to the respective outlets of the sieve bed(s), a compressor operable to pressurize ambient air, one or more sieve bed flow paths from the compressor to respective inlets of the sieve bed(s), a bypass flow path from the compressor to the product tank that bypasses the sieve bed(s), and a valve unit operable to selectively allow flow of pressurized ambient air from the compressor along the one or more sieve bed flow paths and along the bypass flow path in response to a control signal. The valve unit may be controlled in response to a command issued by a ventilator based on a calculated or estimated total flow of gas and entrained air or % FiO₂ of a patient.

20 Claims, 12 Drawing Sheets

Related U.S. Application Data division of application No. 16/874,472, filed on May 14, 2020, now Pat. No. 11,607,519.

(60) Provisional application No. 62/851,204, filed on May 22, 2019.

(51) Int. Cl.
*A61M 16/10* (2006.01)
*A61M 16/20* (2006.01)

(52) U.S. Cl.
CPC ........... *A61M 16/20* (2013.01); *B01D 53/047* (2013.01); *A61M 2202/0208* (2013.01); *A61M 2202/0266* (2013.01); *A61M 2205/3337* (2013.01); *B01D 2253/108* (2013.01); *B01D 2256/12* (2013.01); *B01D 2257/102* (2013.01)

(58) Field of Classification Search
CPC .. A61M 2202/0266; A61M 2205/3337; A61M 16/024; A61M 16/105; A61M 16/201; A61M 16/203; A61M 16/208; A61M 2016/0027; A61M 2016/0039; A61M 2016/1025; A61M 2205/3331; A61M 2205/3334; A61M 2205/3561; A61M 2205/3592; A61M 2205/50; A61M 2205/502; A61M 2205/75; A61M 2205/8206; A61M 2209/086; A61M 16/0003; A61M 16/107; A61M 2016/0036; B01D 53/047; B01D 53/04; B01D 2253/108; B01D 2256/12; B01D 2257/102; B01D 2259/4533; B01D 53/0407; B01D 53/053
USPC .............. 95/8, 11, 19, 23, 130; 96/109, 111, 96/113–116, 121; 128/204.18, 204.21, 128/204.22, 204.26, 205.11, 205.24
See application file for complete search history.

(56) References Cited

U.S. PATENT DOCUMENTS

| | | | |
|---|---|---|---|
| 4,870,960 A | 10/1989 | Hradek | |
| 5,626,131 A | 5/1997 | Chua et al. | |
| 6,605,136 B1 | 8/2003 | Graham et al. | |
| 6,640,463 B1 | 11/2003 | Beck et al. | |
| 6,824,590 B2 | 11/2004 | Dee et al. | |
| 7,066,985 B2 | 6/2006 | Deane et al. | |
| 7,135,059 B2 | 11/2006 | Deane et al. | |
| 7,279,029 B2 | 10/2007 | Occhialini et al. | |
| 7,438,745 B2 | 10/2008 | Deane et al. | |
| 7,473,299 B2 | 1/2009 | Occhialini et al. | |
| 7,585,351 B2 | 9/2009 | Deane et al. | |
| 7,686,870 B1 | 3/2010 | Deane et al. | |
| 7,708,802 B1 | 5/2010 | Deane et al. | |
| 7,730,887 B2 | 6/2010 | Deane et al. | |
| 7,753,996 B1 | 7/2010 | Deane et al. | |
| 7,780,768 B2 | 8/2010 | Taylor et al. | |
| 7,841,343 B2 | 11/2010 | Deane et al. | |
| 7,857,894 B2 | 12/2010 | Taylor et al. | |
| 7,922,789 B1 | 4/2011 | Deane et al. | |
| 8,142,544 B2 | 3/2012 | Taylor et al. | |
| 8,366,815 B2 | 2/2013 | Taylor et al. | |
| 8,377,181 B2 | 2/2013 | Taylor et al. | |
| 8,440,004 B2 | 5/2013 | Taylor et al. | |
| 8,568,519 B2 | 10/2013 | Taylor et al. | |
| 8,580,015 B2 | 11/2013 | Taylor et al. | |
| 8,702,841 B2 | 4/2014 | Taylor et al. | |
| 9,220,864 B2 | 12/2015 | Taylor et al. | |
| 9,283,346 B2 | 3/2016 | Taylor et al. | |
| 9,592,360 B2 | 3/2017 | Taylor et al. | |
| 9,907,926 B2 | 3/2018 | Allum | |
| 9,995,645 B2 | 6/2018 | Allum | |
| 10,004,869 B2 | 6/2018 | Taylor et al. | |
| 10,080,521 B2 | 9/2018 | Parrish | |
| 10,265,493 B2 | 4/2019 | Heatherington et al. | |
| 10,384,028 B2 | 8/2019 | Allum et al. | |
| 2005/0045041 A1 | 3/2005 | Hechinger et al. | |
| 2005/0072423 A1 | 4/2005 | Deane et al. | |
| 2005/0072426 A1 | 4/2005 | Deane et al. | |
| 2006/0090759 A1 | 5/2006 | Howes et al. | |
| 2006/0124128 A1 | 6/2006 | Deane et al. | |
| 2006/0292654 A1 | 12/2006 | Reardon | |
| 2008/0072907 A1 | 3/2008 | Deane et al. | |
| 2008/0110338 A1 | 5/2008 | Taylor et al. | |
| 2008/0202337 A1 | 8/2008 | Taylor et al. | |
| 2008/0276939 A1 | 11/2008 | Tiedje | |
| 2009/0126736 A1 | 5/2009 | Taylor et al. | |
| 2009/0131763 A1 | 5/2009 | Taylor et al. | |
| 2012/0272966 A1* | 11/2012 | Ando | B01D 53/30 128/205.27 |
| 2013/0061750 A1 | 3/2013 | Makihira et al. | |
| 2013/0110416 A1 | 5/2013 | Hill | |
| 2014/0261426 A1 | 9/2014 | Ahmad | |
| 2015/0196727 A1 | 7/2015 | Ahmad | |
| 2016/0107116 A1* | 4/2016 | Metrulas | B64D 37/32 95/1 |
| 2017/0072159 A1 | 3/2017 | Romano et al. | |
| 2017/0113013 A1 | 4/2017 | Allum | |
| 2017/0143926 A1 | 5/2017 | Allum et al. | |
| 2017/0340851 A1 | 11/2017 | Allum et al. | |
| 2017/0348501 A1 | 12/2017 | Taylor et al. | |
| 2017/0361052 A1 | 12/2017 | Taylor et al. | |
| 2018/0001048 A1 | 1/2018 | Allum | |
| 2018/0110954 A1 | 4/2018 | Belisario et al. | |
| 2018/0185602 A1 | 7/2018 | Edwards | |
| 2018/0200474 A1 | 7/2018 | Allum et al. | |
| 2018/0200475 A1 | 7/2018 | Allum et al. | |
| 2018/0364119 A1 | 12/2018 | Allum | |
| 2018/0369531 A1 | 12/2018 | Taylor et al. | |
| 2019/0054265 A1 | 2/2019 | Shahar et al. | |
| 2019/0070374 A1 | 3/2019 | Fogarty | |
| 2019/0099570 A1 | 4/2019 | Brambilla et al. | |
| 2019/0175860 A1 | 6/2019 | Allum et al. | |
| 2019/0344033 A1 | 11/2019 | Ahmad | |
| 2020/0398013 A1 | 12/2020 | Hete et al. | |
| 2021/0113747 A1 | 4/2021 | Bullock et al. | |
| 2021/0236757 A1* | 8/2021 | Vicario | A61M 16/085 |
| 2021/0346634 A1* | 11/2021 | Martin | A61M 16/101 |
| 2023/0181861 A1 | 6/2023 | Westfall et al. | |

FOREIGN PATENT DOCUMENTS

| | | |
|---|---|---|
| CN | 103314187 A | 9/2013 |
| EP | 978477 A1 | 2/2000 |
| JP | 63079710 A | 4/1988 |
| JP | 2008081371 A | 4/2008 |
| JP | 2011502547 A | 1/2011 |
| JP | 2012519542 | 2/2016 |
| KR | 1020090057520 A | 6/2009 |
| WO | 2008052364 A1 | 5/2008 |
| WO | 2010115166 A1 | 10/2010 |
| WO | 2015058036 A1 | 4/2015 |
| WO | 2019070136 | 4/2019 |
| WO | 2020154700 A1 | 7/2020 |

OTHER PUBLICATIONS

Japanese Office Action for JP2020-086518; mailed Jul. 6, 2021.
European Search Report for EP 20175818; mailed Oct. 5, 2020.
Japanese Office Action for Japanese Patent Application No. 2022-084992; mailed Feb. 21, 2023.
Partial European Search Report for EP 22 20 4541; mailed Feb. 9, 2023.
Examination Report for European Patent Application No. 22204541. 1; mailed Oct. 22, 2024.
Chinese Office Action for Application No. 2023105326961; mailed Jul. 12, 2025.

(56) References Cited

OTHER PUBLICATIONS

Second Chinese Office Action for Application No. 2023105326961; mailed Feb. 8, 2026.

* cited by examiner

CPAP AIR INLET

630

600

610

620

STORE PATIENT INTERFACE CONSTANTS — 802

MEASURE FLOW OF GAS FROM NOZZLE — 804

MEASURE PRESSURE IN PATIENT INTERFACE — 806

CALCULATE TOTAL FLOW — 808

CALCULATE INSPIRED TIDAL VOLUME(S) — 810

CALCULATE %FiO$_2$ — 812

TRANSMIT SIGNAL TO O$_2$ CONCENTRATOR — 814

O₂ CONCENTRATOR WITH SIEVE BED BYPASS AND CONTROL METHOD THEREOF

CROSS-REFERENCE TO RELATED APPLICATIONS

This application is a continuation of U.S. patent application Ser. No. 18/109,560, filed Feb. 14, 2023 and entitled "O2 CONCENTRATOR WITH SIEVE BED BYPASS AND CONTROL METHOD THEREOF," which is a divisional of U.S. patent application Ser. No. 16/874,472, filed May 14, 2020 and entitled "O2 CONCENTRATOR WITH SIEVE BED BYPASS AND CONTROL METHOD THEREOF," issued as U.S. Pat. No. 11,607,519 on Mar. 21, 2023, which relates to and claims the benefit of U.S. Provisional Application No. 62/851,204 filed May 22, 2019 and entitled "O2 CONCENTRATOR WITH SIEVE BED BYPASS AND CONTROL METHOD THEREOF," the entire disclosure of each of which is hereby wholly incorporated by reference.

STATEMENT RE: FEDERALLY SPONSORED RESEARCH/DEVELOPMENT

Not Applicable

BACKGROUND

1. Technical Field of the Invention

The present disclosure relates generally to oxygen concentrators and, more particularly, to an oxygen concentrator arranged to produce a high oxygen content gas to be delivered to a patient by a ventilator.

2. Description of the Related Art

A wide range of clinical conditions may require some form of ventilation therapy, whereby the patient's work of breathing is assisted by the flow of pressurized gas from a ventilator to the patient's airway. These conditions may include hypoxemia, various forms of respiratory insufficiency, and airway disorders. There are also non-respiratory and non-airway diseases that require ventilation therapy, such as congestive heart failure and neuromuscular diseases.

To improve the quality of life of many patients who require long-term ventilation therapy, ventilation systems have been developed which are miniaturized and portable. Some of these systems, for example, the Life2000® system by Breathe Technologies, Inc., are so lightweight and compact that in their extended range or stand-alone configurations, they are wearable by the patient. These systems make use of a source of pressurized ventilation gas to operate. In the stationary or extended-range configuration, the source of pressurized gas may be a stationary compressor unit, which may be kept in a patient's home. In the stand-alone configuration, which may be generally used when the patient is outside the home, the portable, wearable ventilator generally receives its ventilation gas from a pressurized gas cylinders or a portable compressor.

Many of the above clinical conditions and other clinical conditions may also require or benefit from supplemental oxygen therapy, whereby the gas introduced to the patient's airway is augmented by the presence of additional oxygen such that the patient inspires gas having oxygen levels above atmospheric concentration (20.9% at 0% humidity). Supplemental oxygen therapy involves the patient receiving supplemental oxygen gas from an oxygen gas source, which is typically a compressed or cryogenic oxygen cylinder, or an oxygen gas generator. For many years, patients who wished to be mobile relied on oxygen cylinders. However, in recent years, miniaturization and improvements in battery technology has resulted in the development of portable oxygen concentrators.

Portable oxygen concentrators typically operate by pressure swing adsorption (PSA), in which ambient air is pressurized by a compressor and passed through an adsorbent sieve bed. The sieve bed is typically formed of a zeolite which preferentially adsorbs nitrogen when at high pressure while oxygen passes through. Once the sieve bed reaches its capacity to adsorb nitrogen, the pressure can be reduced. This reduction in pressure causes the adsorbed nitrogen to be desorbed so it can be purged, leaving a regenerated sieve bed that is again ready to adsorb nitrogen. With repeated cycles of this operation, an enriched oxygen gas may be generated. Typically, portable oxygen concentrators have at least two sieve beds so that at one may operate while the other is being purged of the nitrogen and vented. Typical portable oxygen concentrators today output an enriched oxygen gas with a purity of around 87-96% oxygen. Among existing oxygen concentrators today which may be considered portable (especially by an individual suffering from a respiratory condition), there are generally two types available. The first type, which is larger and heavier, is usually capable of continuous flow delivery. Models of this type typically weigh between 5-10 kg, have maximum flow rates of around 5-6 liters per minute or less, and are generally configured with wheels and a handle, often mimicking the appearance of a suitcase. The second type are lighter units more suitable for being carried or worn in a satchel, handbag, or a backpack. Models of this type typically weigh less than 2.5 kg and are usually limited to pulsed delivery modes with maximum flow rates of around 2 liters per minute or less.

Portable oxygen concentrators have a substantial cost and convenience advantage over pressurized oxygen cylinders, due to the pressurized oxygen cylinders requiring ongoing refilling or replacement. Additionally, portable oxygen concentrators are considered to be significantly safer than pressurized oxygen cylinders. This safety consideration can have a substantial impact on a patient's quality of life, because many portable oxygen concentrators have been approved by the FAA for use by travelers on commercial airlines, whereas oxygen cylinders are universally banned on commercial flights. Consequently, patients with pressurized oxygen cylinders must make expensive and time-consuming preparations with an airline ahead of time, or forego airline travel entirely.

For patients with conditions where assistance with the work of breathing is not required, supplemental oxygen therapy alone, without ventilation therapy, may be sufficient. However, for many patients, combined ventilation therapy and supplemental oxygen therapy may be a more optimal treatment. In healthy patients, sufficient ventilation to perform the work of breathing may typically require minute ventilation rates of between 5 and 8 L/min while stationary, which may double during light exercise, and which may exceed 40 L/min during heavy exercise. Patients suffering from respiratory conditions may require substantially higher rates, and substantially higher instantaneous rates. This is especially true when these patients are outside the home and require portability, as at these times such patients are often also involved in light exercise.

It may thus be seen that patients who would prefer to receive this combined mode of treatment are substantially limited, due to the fact that in many cases existing portable oxygen concentrators do not output gas at pressures and/or volumes high enough to be used with a wearable, portable ventilator without the presence of an additional source of compressed gas. As such, when maximum portability is desired, these patients must either forego the substantial benefits of a portable oxygen concentrator and return to oxygen cylinders (which may output oxygen gas at the higher pressures and flow rates required for ventilation therapy), or additionally have with them a portable compressor, with the portable oxygen concentrator, the portable compressor, and the wearable ventilator interfaced together.

Existing systems and methods that seek to provide a combined supplemental oxygen/ventilation system are substantially deficient. For example, U.S. Patent Application Pub. Nos. 2017/0340851 and 2018/0001048 describe the addition of an accumulator tank downstream of the product tank of an oxygen concentrator, for the stated purpose of providing a more constant flow of product gas to a mechanical ventilator. U.S. Patent Application Pub. No. 2017/0113013 describes the use of product tank pressure and output flow rate measurements to determine whether the oxygen concentrator is fluidly coupled to a ventilator (which may be characterized by utilization of the oxygen-enriched gas of the oxygen concentrator in intermittent, spontaneous bursts). If it is, the oxygen concentrator's valves or pump is controlled to increase or decrease product tank pressure or gas flow rate to meet the supply gas requirements of the ventilator. Such systems can generally be understood as being aimed only at satisfying the course demands of the ventilator, such as ensuring that the product tank pressure does not fall below a certain threshold. They have no capability of meeting the specific needs of a patient undergoing ventilation therapy. While U.S. Patent Application Pub. No. 2017/0113013 contemplates the determination of a patient status indicator, the determination is based solely on measurements performed within the concentrator and amounts to no more than a rough estimation.

BRIEF SUMMARY

The present disclosure contemplates various systems, methods, and apparatuses for overcoming the above drawbacks accompanying the related art. One aspect of the embodiments of the present disclosure is an oxygen concentrator including one or more adsorbent sieve beds operable to remove nitrogen from air to produce concentrated oxygen gas at respective outlets thereof, a product tank fluidly coupled to the respective outlets of the one or more adsorbent sieve beds, a compressor operable to pressurize ambient air, one or more sieve bed flow paths from the compressor to respective inlets of the one or more adsorbent sieve beds, a bypass flow path from the compressor to the product tank that bypasses the one or more adsorbent sieve beds, and a valve unit operable to selectively allow flow of pressurized ambient air from the compressor along the one or more sieve bed flow paths and along the bypass flow path in response to a control signal.

The valve unit may include one or more ON/OFF valves and the valve unit may selectively allow flow of pressurized ambient air from the compressor along the one or more sieve bed flow paths and along the bypass flow path by selectively adjusting a timing of states of the one or more ON/OFF valves relative to an operation cycle of the one or more adsorbent sieve beds.

The valve unit may include one or more proportional valves and the valve unit may selectively allow flow of pressurized ambient air from the compressor along the one or more sieve bed flow paths and along the bypass flow path by selectively adjusting a magnitude of an input to the one or more proportional valves. The valve unit may further selectively allow flow of pressurized ambient air from the compressor along the one or more sieve bed flow paths and along the bypass flow path by selectively adjusting a timing of states of the one or more proportional valves relative to an operation cycle of the one or more adsorbent sieve beds.

The oxygen concentrator may further include a controller operable to generate the control signal. The control signal generated by the controller may operate the valve unit to maintain a preset oxygen concentration in the product tank. The controller may generate the control signal in response to a command issued by a ventilator fluidly coupled to an outlet of the product tank.

Another aspect of the embodiments of the present disclosure is a system including the above oxygen concentrator and the above ventilator. The ventilator may calculate the preset oxygen concentration based on a user input oxygen concentration. The ventilator may calculate the preset oxygen concentration further based on a measured ventilation gas output of the ventilator. The ventilator may calculate the preset oxygen concentration further based on a measured pressure in a patient ventilation interface of the ventilator.

The ventilator may include a flow sensor for measuring a flow of gas expelled by one or more nozzles of a patient ventilation interface connected to the ventilator, a pressure sensor for measuring a pressure in the patient ventilation interface, and a master controller configured to issue the command based on the measured flow and the measured pressure. The master controller may be configured to issue the command based on a calculation of a total flow of gas and entrained air delivered by the ventilator as a function of the measured pressure and the measured flow. The master controller may be configured to issue the command based on a comparison of the measured pressure to a plurality of measurements of total flow of gas and entrained air delivered by the ventilator stored in correspondence with a plurality of measurements of pressure in the patient ventilation interface for the measured flow. The master controller may be configured to issue the command based on a comparison of the measured pressure to a plurality of measurements of fraction of inspired oxygen % $FiO_2$ stored in correspondence with a plurality of measurements of pressure in the patient ventilation interface for the measured flow.

The control signal generated by the controller may operate the compressor to maintain a preset oxygen concentration in the product tank.

Another aspect of the embodiments of the present disclosure is an oxygen concentrator including one or more adsorbent sieve beds operable to remove nitrogen from air to produce concentrated oxygen gas at respective outlets thereof, a product tank fluidly coupled to the respective outlets of the one or more adsorbent sieve beds, a compressor operable to pressurize ambient air, one or more sieve bed flow paths from the compressor to respective inlets of the one or more adsorbent sieve beds, a bypass compressor operable to pressurize ambient air, the bypass compressor being distinct from the compressor, a bypass flow path from the bypass compressor to the product tank that bypasses the one or more adsorbent sieve beds, and a controller operable to generate a control signal to control the bypass compressor to selectively allow flow of pressurized ambient air from the bypass compressor along the bypass flow path.

Another aspect of the embodiments of the present disclosure is an oxygen concentrator including one or more adsorbent sieve beds operable to remove nitrogen from air to produce concentrated oxygen gas at respective outlets thereof, a product tank fluidly coupled to the respective outlets of the one or more adsorbent sieve beds, a compressor operable to pressurize ambient air, one or more sieve bed flow paths from the compressor to respective inlets of the one or more adsorbent sieve beds, a bypass flow path from an external compressor fluid port to the product tank that bypasses the one or more adsorbent sieve beds, and a controller operable to generate a control signal to control, via an external compressor signal port, an external compressor in fluid communication with the external compressor fluid port, the control signal selectively allowing flow of pressurized ambient air from the external compressor along the bypass flow path.

Another aspect of the embodiments of the present disclosure is a modular system including the above oxygen concentrator, an oxygen concentrator module housing the oxygen concentrator, and a compressor module housing the external compressor. The oxygen concentrator module and the compressor module may be detachably attachable to from a single unit.

Another aspect of the embodiments of the present disclosure is a method for controlling an oxygen concentrator to meet a patient's ventilation and supplemental oxygen needs at a plurality of activity levels of the patient. The method may include transitioning the oxygen concentrator to a first configuration in which a first portion of ambient air equal to or greater than no ambient air mixes with concentrated oxygen gas output by one or more sieve beds of the oxygen concentrator to produce a concentrator output at a first flow having a first oxygen concentration. The method may further include transitioning the oxygen concentrator to a second configuration in which a second portion of ambient air greater than the first portion mixes with the concentrated oxygen gas output by the one or more sieve beds to produce a concentrator output at a second flow having a second oxygen concentration, the second flow being greater than the first flow and the second oxygen concentration being less than the first oxygen concentration.

Another aspect of the embodiments of the present disclosure is a method for controlling an oxygen concentrator to meet a patient's ventilation and supplemental oxygen needs at a plurality of activity levels of the patient. The method may include transitioning the oxygen concentrator to a first configuration in which a first portion of concentrated oxygen gas output by one or more sieve beds of the oxygen concentrator, the first portion being equal to or greater than no concentrated oxygen gas, mixes with ambient air to produce a concentrator output at a first flow having a first oxygen concentration. The method may further include transitioning the oxygen concentrator to a second configuration in which a second portion of concentrated oxygen gas output by the one or more sieve beds, the second portion being greater than the first portion, mixes with the ambient air to produce a concentrator output at a second flow having a second oxygen concentration, the second flow being less than the first flow and the second oxygen concentration being greater than the first oxygen concentration.

Another aspect of the embodiments of the present disclosure is a method for calculating a total flow of gas and entrained air delivered by a ventilator to a patient. The method may include storing one or more constants in association with each of a plurality of nozzle geometries, measuring a flow of gas expelled by one or more nozzles of a patient ventilation interface connected to the ventilator, the one or more nozzles having a nozzle geometry corresponding to one of the plurality of nozzle geometries, measuring a pressure in the patient ventilation interface, and calculating the total flow based on the measured flow, the measured pressure, and the one or more constants stored in association with the nozzle geometry of the one or more nozzles.

The method may further include transmitting a signal to an oxygen concentrator based on the calculated total flow.

The method may further include calculating a total inspired tidal volume by integrating the calculated total flow with respect to time. The method may further include transmitting a signal to an oxygen concentrator based on the calculated total inspired tidal volume.

The method may further include calculating an inspired tidal volume of the gas expelled by the one or more nozzles by integrating the measured flow with respect to time, calculating an inspired tidal volume of entrained air by integrating an entrained flow with respect to time, the entrained flow being the difference between the calculated total flow and the measured flow, and calculating a fraction of inspired oxygen % $FiO_2$ of the patient based on the inspired tidal volume of the gas expelled by the one or more nozzles and the inspired tidal volume of entrained air. The method may further include transmitting a signal to an oxygen concentrator based on the calculated % $FiO_2$.

For each of the plurality of nozzle geometries, the associated one or more constants are stored in a memory disposed in a patient ventilation interface with a nozzle having that nozzle geometry. Calculating the total flow may include reading the one or more constants stored in the patient ventilation interface connected to the ventilator.

Another aspect of the embodiments of the present disclosure is a method for controlling an oxygen concentrator based on a total flow of gas and entrained air delivered by a ventilator to a patient. The method may include measuring a flow of gas expelled by one or more nozzles of a patient ventilation interface connected to the ventilator, measuring a pressure in the patient ventilation interface, calculating the total flow based on the measured flow and the measured pressure, and transmitting a signal to the oxygen concentrator based on the calculated total flow.

The method may further include calculating a total inspired tidal volume by integrating the calculated total flow with respect to time. The transmitting of the signal may be based on the calculated total inspired tidal volume.

The method may further include calculating an inspired tidal volume of the gas expelled by the one or more nozzles by integrating the measured flow with respect to time, calculating an inspired tidal volume of entrained air by integrating an entrained flow with respect to time, the entrained flow being the difference between the calculated total flow and the measured flow, and calculating a fraction of inspired oxygen % $FiO_2$ of the patient based on the inspired tidal volume of the gas expelled by the one or more nozzles and the inspired tidal volume of entrained air. The transmitting of the signal may be based on the calculated % $FiO_2$.

Another aspect of the embodiments of the present disclosure is a non-transitory program storage medium on which are stored instructions executable by a processor or programmable circuit to perform operations for controlling an oxygen concentrator based on a total flow of gas and entrained air delivered by a ventilator to a patient. The operations may include measuring a flow of gas expelled by one or more nozzles of a patient ventilation interface connected to the ventilator, measuring a pressure in the patient ventilation interface, and calculating the total flow based on the measured flow and the measured pressure.

Another aspect of the embodiments of the present disclosure is a ventilator including the above non-transitory program storage medium, a processor or programmable circuit for executing the instructions, a flow sensor, and a pressure sensor. Measuring the flow may include communicating with the flow sensor, and measuring the pressure may include communicating with the pressure sensor.

Another aspect of the embodiments of the present disclosure is a ventilation system including the above ventilator and an oxygen concentrator connected to the ventilator. The operations may further include transmitting a signal from the ventilator to the oxygen concentrator based on the calculated total flow.

The oxygen concentrator may include a controller operable to generate a control signal in response to the signal transmitted from the ventilator, the control signal generated by the controller selectively allowing flow of pressurized ambient air into a product tank of the oxygen concentrator. The control signal generated by the controller may operate a valve unit of the oxygen concentrator to maintain a preset oxygen concentration in the product tank according to the signal transmitted from the ventilator. The control signal generated by the controller may operate the valve unit to allow the flow of pressurized ambient air to bypass one or more sieve beds of the oxygen concentrator. The control signal generated by the controller may operate a compressor of the oxygen concentrator to maintain a preset oxygen concentration in the product tank according to the signal transmitted from the ventilator. The control signal generated by the controller may operate a compressor external to the oxygen concentrator to maintain a preset oxygen concentration in the product tank according to the signal transmitted from the ventilator.

Another aspect of the embodiments of the present disclosure is a method for controlling an oxygen concentrator to meet a patient's ventilation and supplemental oxygen needs at a plurality of activity levels of the patient. The method may include transitioning the oxygen concentrator to a first configuration in which a first portion of ambient air mixes with concentrated oxygen gas output by one or more sieve beds of the oxygen concentrator to produce a concentrator output at a first flow having a first oxygen concentration. The method may further include transitioning the oxygen concentrator to a second configuration in which a second portion of ambient air mixes with the concentrated oxygen gas output by the one or more sieve beds to produce a concentrator output at a second flow having a second oxygen concentration, the second flow being greater than the first flow and the second oxygen concentration being less than the first oxygen concentration.

Another aspect of the embodiments of the present disclosure is a method for estimating a total flow of gas and entrained air delivered by a ventilator to a patient. The method may include storing, for each of a plurality of measurements of a flow of gas expelled by one or more nozzles of a patient ventilation interface connected to the ventilator, a plurality of measurements of total flow in correspondence with a plurality of measurements of pressure in the patient ventilation interface, measuring a flow of gas expelled by the one or more nozzles, measuring a pressure in the patient ventilation interface, and estimating the total flow based on a comparison of the measured pressure to the plurality of measurements of total flow stored for the measured flow.

The method may further include transmitting a signal to an oxygen concentrator based on the estimated total flow.

The method may further include calculating a fraction of inspired oxygen % $FiO_2$ of the patient based on a percentage of oxygen included in the gas expelled by the one or more nozzles and the estimated total flow. The method may further include transmitting a signal to an oxygen concentrator based on the calculated % $FiO_2$.

Another aspect of the embodiments of the present disclosure is a method for estimating a fraction of inspired oxygen % $FiO_2$ of a patient receiving ventilatory support from a ventilator. The method may include storing, for each of a plurality of measurements of a flow of gas expelled by one or more nozzles of a patient ventilation interface connected to the ventilator, a plurality of measurements of % $FiO_2$ in correspondence with a plurality of measurements of pressure in the patient ventilation interface, measuring a flow of gas expelled by the one or more nozzles, measuring a pressure in the patient ventilation interface, and estimating the % $FiO_2$ of the patient based on a comparison of the measured pressure to the plurality of measurements of % $FiO_2$ stored for the measured flow.

The method may further include transmitting a signal to an oxygen concentrator based on the estimated % $FiO_2$.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure encompasses various embodiments of oxygen concentrators, ventilators, and control systems and methods thereof. The detailed description set forth below in connection with the appended drawings is intended as a description of several currently contemplated embodiments and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
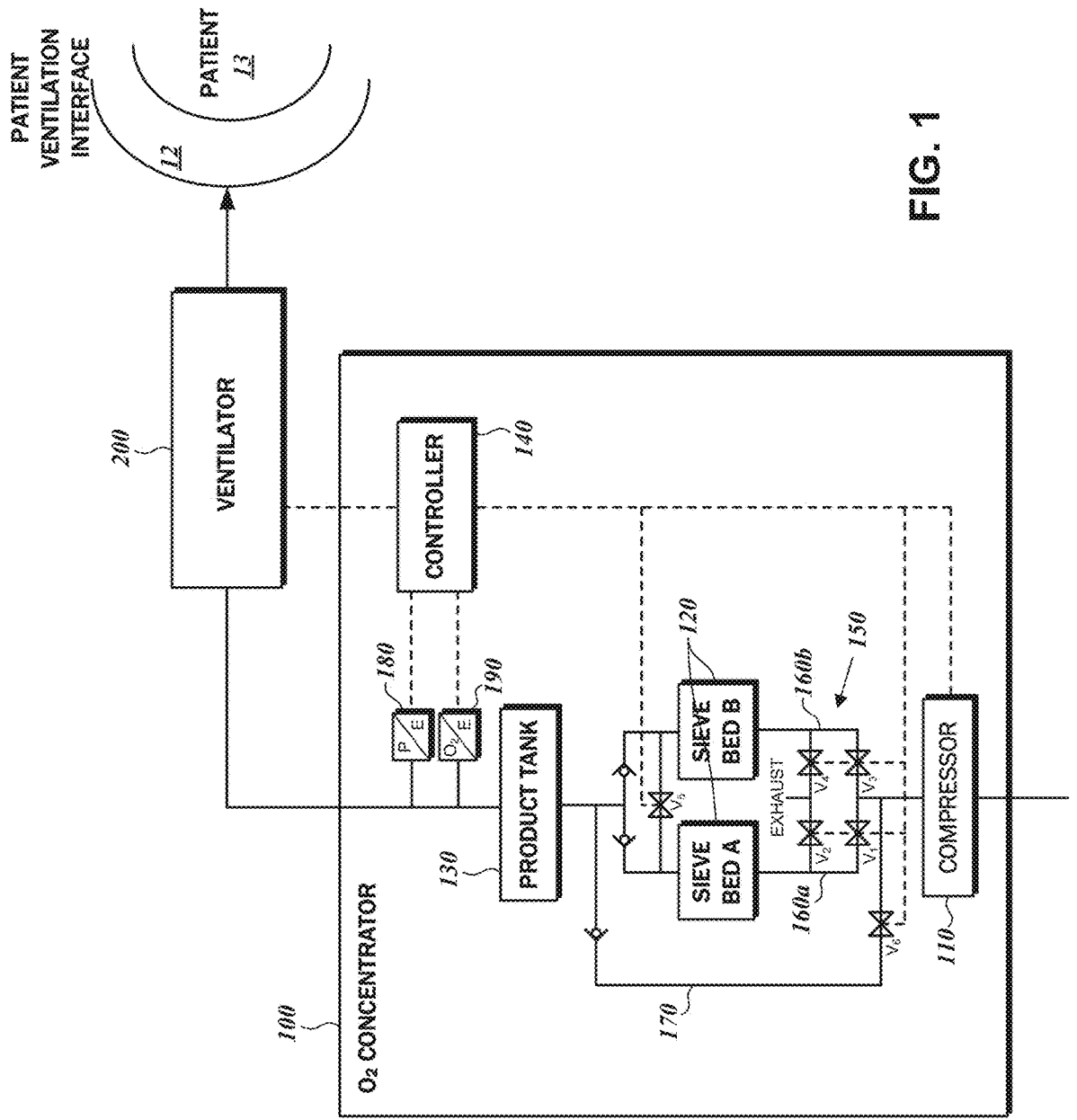
FIG. 1 shows an example oxygen concentrator according to an embodiment of the present disclosure.

FIG. 1 shows an example oxygen concentrator 100 according to an embodiment of the present disclosure. As shown, a ventilator 200 is arranged to deliver a high oxygen content gas produced by the oxygen concentrator 100 to a patient 13 via a patient ventilation interface 12. Depending on various factors including, for example, the prescription of the patient 13, the patient's activity level, user-adjustable settings, and the state of the patient's breathing in a given moment, the ventilator 200 may instruct the oxygen concentrator 100 to produce a specific flow (e.g. volume flow) of gas having a specific oxygen concentration. The ventilator 200 may then provide such high oxygen content gas to the patient 13 via the patient ventilation interface 12 such that, taking into account any entrainment of additional ambient air in the patient ventilation interface 12, the patient 13 is provided with a desired degree of assistance to the patient's work of breathing and a target $FiO_2$.

In general, in order to produce the high oxygen content gas from ambient air, a compressor 110 of the oxygen concentrator 100 pumps ambient air through one or more adsorbent sieve beds 120 that remove nitrogen from the pressurized air. The resulting gas having high oxygen concentration (e.g. >90%) flows into a product tank 130 for delivery to the ventilator 200. In more detail, a controller 140 of the oxygen concentrator 100 may control a valve unit 150 in order to cyclically bring pressurized ambient air into the sieve bed(s) 120 and exhaust the nitrogen waste product extracted by the sieve bed(s). As shown in FIG. 1, for example, two sieve beds 120 may be provided (e.g. Sieve Bed A and Sieve Bed B) having opposed operation cycles, Sieve Bed A filling the product tank 130 with high oxygen content gas at the same time that Sieve Bed B is exhausting nitrogen to ambient and vice versa.

The present disclosure contemplates various ways of modifying and/or supplementing such processes in order to finely tune the oxygen concentrator 100 to produce a desired flow of gas at a specific oxygen concentration. Such an oxygen concentrator 100 may be used together with the ventilator 200 to meet the changing needs of the patient 13 in real time.

Referring more closely to the arrangement of valves and conduits of the valve unit 150, it can be seen that the example oxygen concentrator 100 of FIG. 1 provides a first sieve bed flow path 160a from the compressor 110 to an inlet of Sieve Bed A through valve $V_1$ of the valve unit 150 and a second sieve bed flow path 160b from the compressor 110 to an inlet of Sieve Bed B through valve $V_3$ of the valve unit 150. In addition to these sieve bed flow paths 160a, 160b, the oxygen concentrator 100 further includes a bypass flow path 170 from the compressor 110 to the product tank 130 through valve $V_6$ of the valve unit 150 that bypasses the one or more sieve beds 120. By controlling valve $V_6$, the controller 140 may allow pressurized ambient air from the compressor 110 to flow directly to the product tank 130 without first passing through the sieve bed(s) 120. Such ambient air, which avoids the pressure drop associated with the sieve bed(s) 120, may then mix with the high oxygen content gas output from the sieve bed(s) 120 in the product tank 130. In comparison to filling the product tank 130 solely from the sieve bed(s) 120, the mixture of ambient air and sieve bed output may accumulate more quickly in the product tank 130 due to the additional volume of ambient air flowing through the bypass flow path 170, while at the same time having a lower oxygen concentration. By appropriately controlling the valve unit 150, the controller 140 may selectively control the rate of flow into the product tank 130 and the oxygen concentration of the resulting product gas in order to meet the needs of the ventilator 200.

For example, the compressor of a conventional oxygen concentrator having no bypass flow path 170 may be required to generate approximately 10 times the flow needed at the output of the oxygen concentrator in order to achieve 93% oxygen concentration. That is, a 2 L/min oxygen concentrator may need to generate 20 L/min of compressed gas in order to produce 2 L/min of oxygen. By using the bypass flow path 170, the oxygen concentrator 100 of the present disclosure may allow for a tradeoff between the oxygen concentration delivered and the continuous flow (e.g. minute ventilation) that the oxygen concentrator 100 can deliver. For example, instead of delivering 2 L/min of flow, the oxygen concentrator 100 may be set to deliver 3.8 L/min of flow with 1.8 L/min of oxygen (via the sieve beds 120) and 2 L/min of ambient air (via the bypass valve 170). The oxygen concentration of the delivered gas will drop down to roughly 60% but the total flow will increase to 3.8 L/min. Using a downstream ventilator 200 that amplifies this flow with entrained air at a ratio of approximately 3:1, the oxygen concentrator 100 can thus deliver a minute volume of 11.4 L/min (3*3.8) with a % $FiO_2$ of about 32%. In comparison, when delivering 2 L/min of 93% oxygen, the oxygen concentrator 100 amplified by the ventilator 200 would only deliver 6 L/min (3*2) but at an $FiO_2$ of 50% to the patient 13. In this way, the oxygen concentrator 100 may produce up to 20 L/min of air (completely bypassing the sieve beds 120), which may then be amplified by the ventilator 200 to 60 L/min (20*3) at an $FiO_2$ of about 21% (the oxygen concentration of ambient air). This may allow a small oxygen concentrator 100 to meet the minute level demands of a very active patient 13. As a patient's activity level goes up, it may be better to provide more ventilation and less oxygen rather than delivering more oxygen. By using the bypass flow path 170, the oxygen concentrator 100 may vary the total gas output between, for example, 2 L/min and 20 L/min, with the oxygen concentration varying accordingly from around 93% to around 21%. The oxygen concentrator 100 may thus act as both a compressor and an oxygen concentrator, with the titration levels controllable by the ventilator 200 as described below.

The controller 140 may control the valve unit 150 by generating a control signal for controlling the individual valves (e.g. $V_1$-$V_6$) of the valve unit 150. For example, the control signal may be generated in response to a command issued by the ventilator 200. In this case, the valve unit 150 may be controlled according to a master/slave arrangement with the ventilator 200 functioning as master and the controller 140 or oxygen concentrator 100 functioning as slave. The ventilator 200 may derive a set point for flow and/or oxygen concentration (e.g. based on inputs such as the prescription of the patient 13, the patient's activity level, user-adjustable settings, and the state of the patient's breathing as measured by the ventilator 200) and the controller 140 may appropriately generate the control signal to achieve that set point. In generating the control signal, the controller 140 may further take into account measurements of a pressure sensor 180 and/or an oxygen concentration sensor 190 fluidly coupled to the outlet of the product tank 130. Such measurements may be fed back to the controller 140 and used as additional inputs along with the set point from the ventilator 200. The controller 140 may, for example, function as a proportional integral derivative (PID) controller or implement other known control loop feedback mechanisms.

Figure 2:
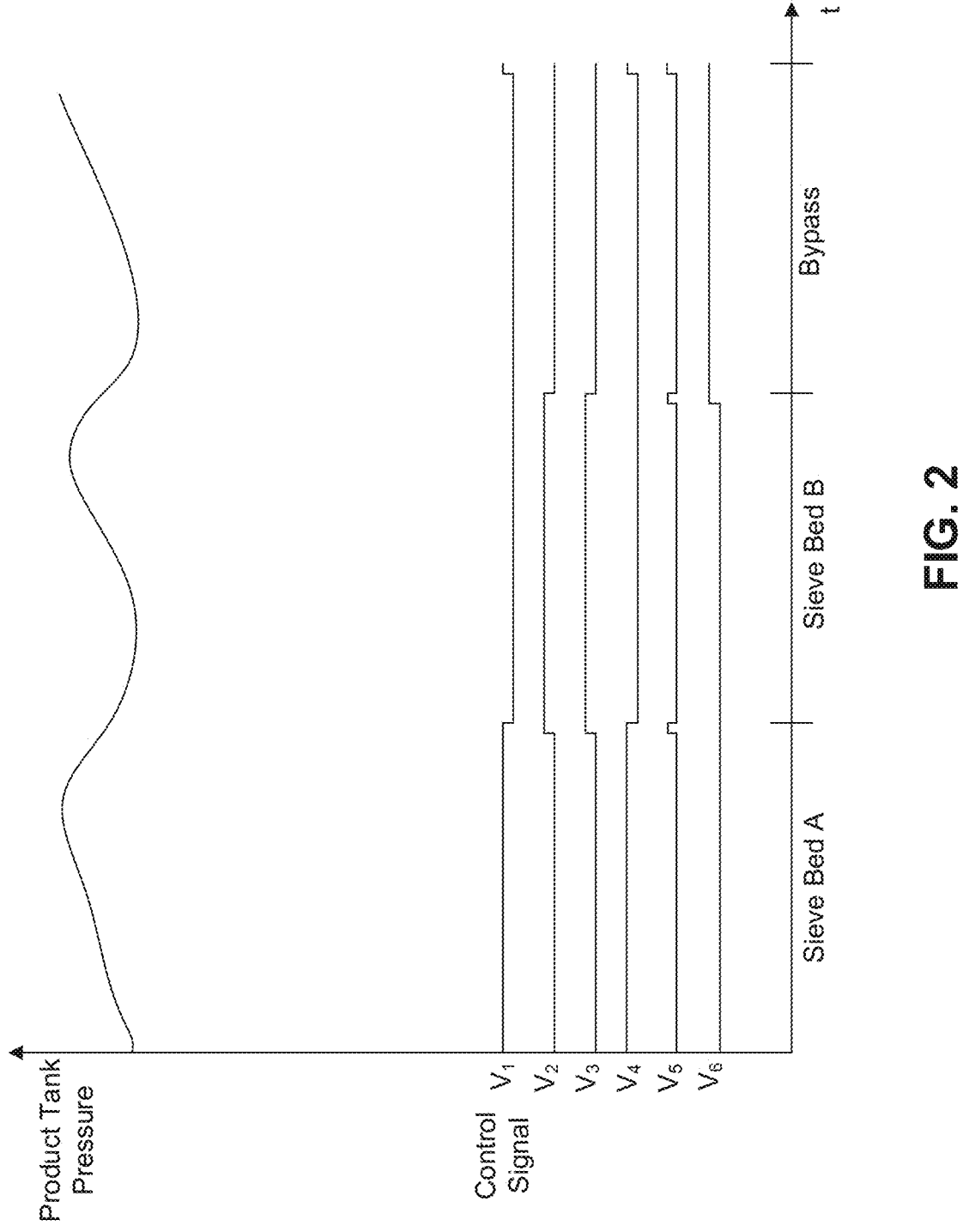
FIG. 2 shows an example control signal for controlling a valve unit of the oxygen concentrator in a case of a bypass flow path including an ON/OFF valve.

FIG. 2 shows an example control signal for controlling the valve unit 150 in a case where the bypass flow path 170 includes an ON/OFF valve $V_6$. In the example of FIG. 2, the valve unit 150 is controlled to implement a three-stage cycle, in which the compressed air from the compressor 110 is passed through Sieve Bed A in a first stage, passed through Sieve Bed B in a second stage, and passed directly to the product tank 130 via the ON/OFF valve $V_6$ and the bypass flow path 170 in a third stage.

Figure 3:
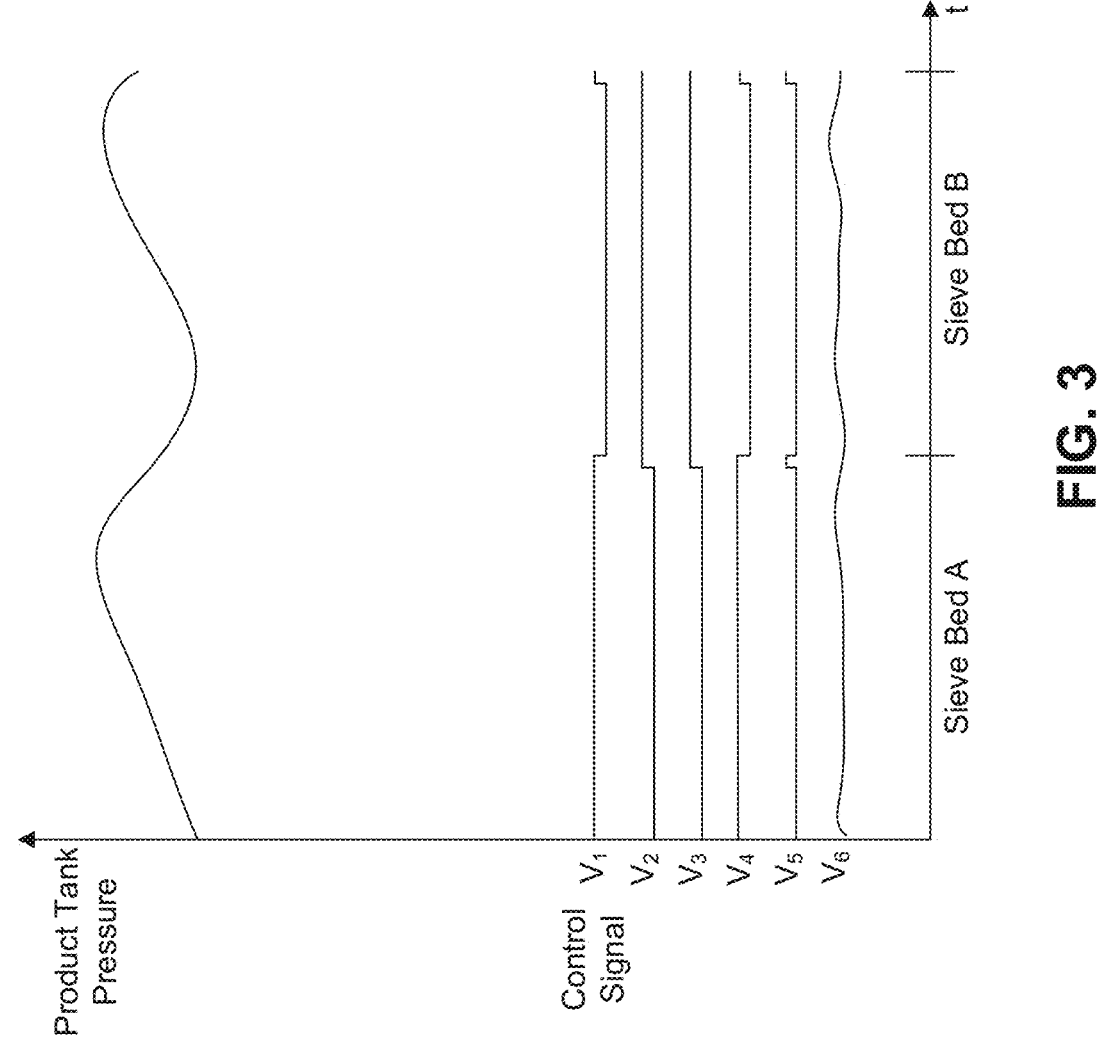
FIG. 3 shows an example control signal for controlling a valve unit of the oxygen concentrator in a case of a bypass flow path including a proportional valve.

FIG. 3 shows an example control signal for controlling the valve unit 150 in a case where the bypass flow path 170 includes a proportional valve $V_6$. In the example of FIG. 3, the valve unit 150 is controlled to implement a two-stage cycle, in which the compressed air from the compressor 110 is passed through Sieve Bed A in a first stage and passed through Sieve Bed B in a second stage, with the proportional valve $V_6$ all the while controlled to selectively allow a portion of the compressed air to pass directly to the product tank 130 via the bypass flow path 170.

In the example described with respect to FIGS. 1-3, the bypass flow path 170 connects the product tank 130 directly to the compressor 110, that is, the same compressor 110 that is fluidly coupled to the sieve beds 120. However, the disclosed subject matter is not intended to be so limited. For example, the bypass flow path 170 may instead extend from a separate, dedicated bypass compressor that is distinct from the compressor 110. Such a dedicated bypass compressor may be turned on and off or the output (e.g. rpm) of the dedicated compressor may be adjusted according to the control signal generated by the controller 140 in order to selectively allow flow from the dedicated bypass compressor to the product tank 150 to achieve the same effect as the valve $V_6$ of the valve unit 150. In the case of controlling a dedicated bypass compressor in this way, the valve $V_6$ may be omitted. The dedicated bypass compressor may be included in the housing of the oxygen concentrator 100 or may be a separate, add-on component whose output is connected to the bypass flow path 170 of the oxygen concentrator 100 via a dedicated connector.

Figure 4:
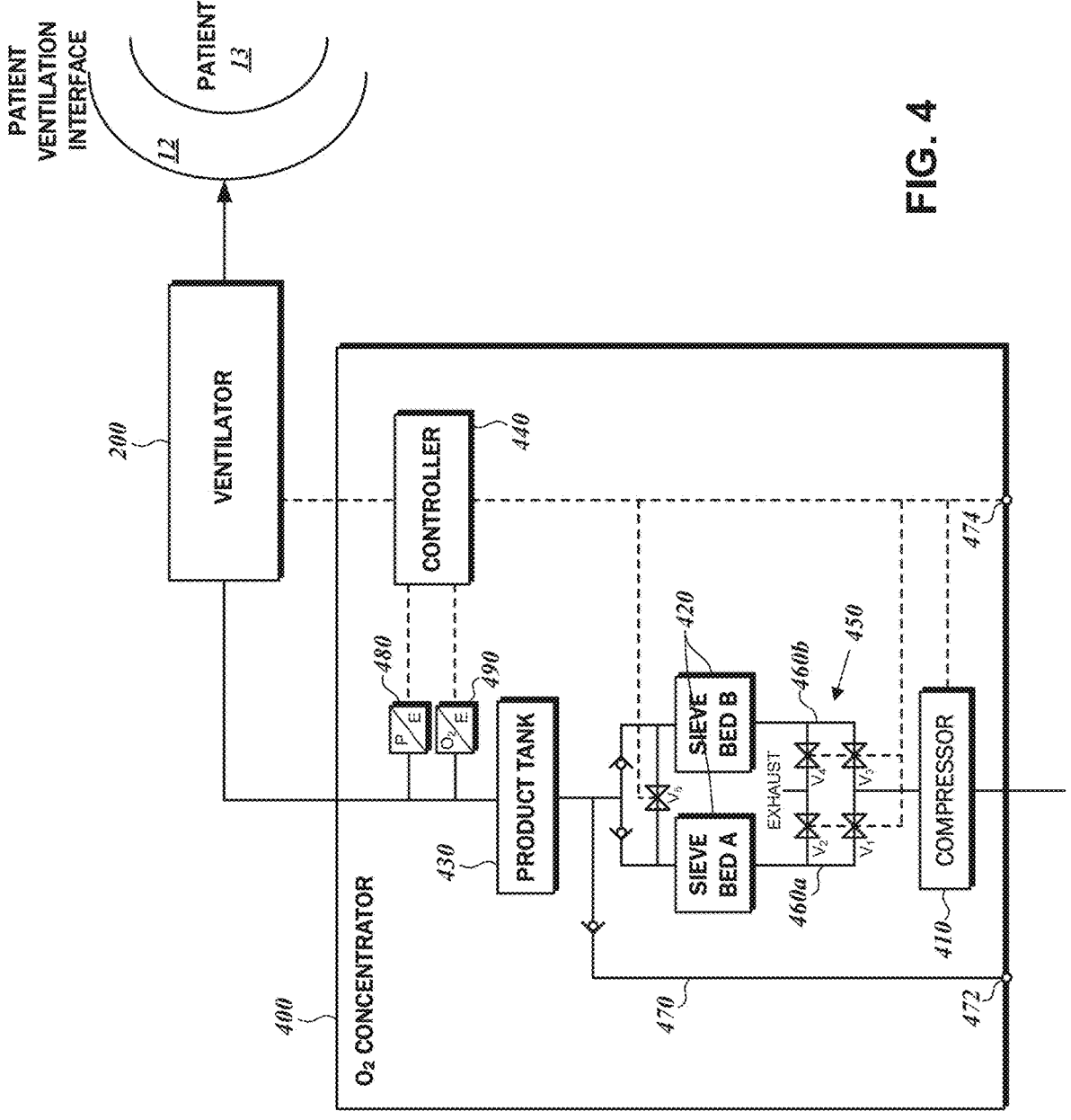
FIG. 4 shows an example of an oxygen concentrator for use with a dedicated bypass compressor that is a separate, add-on component.

FIG. 4 shows an example of an oxygen concentrator 400 for use with a dedicated bypass compressor that is a separate, add-on component as described above. The oxygen concentrator 400 may be the same as the oxygen concentrator 100 described in relation to FIG. 1 and may include a compressor 410, sieve beds 420, product tank 430, controller 440, valve unit 450, sieve bed flow paths 460*a*, 460*b*, bypass flow path 470, pressure sensor 480, and oxygen concentration sensor 490 that are the same as the compressor 110, sieve beds 120, product tank 130, controller 140, valve unit 150, sieve bed flow paths 160*a*, 160*b*, bypass flow path 170, pressure sensor 180, and oxygen concentration sensor 190 of the oxygen with the following differences. Whereas the bypass flow path 170 of FIG. 1 extends from the compressor 110 to the product tank 130, the bypass flow path 470 of FIG. 4 does not extend from the compressor 410 to the product tank 430 but rather extends from an external compressor fluid port 472 to the product tank 430. Furthermore, valve $V_6$ of the valve unit 150 is omitted in the valve unit 450 and the control signal generated by the controller

440 is instead used to control the external bypass compressor via an external compressor signal port 474. As noted above, such an external bypass compressor may be turned on and off or the output of the external compressor may be adjusted according to the control signal in order to achieve the same effect as the valve $V_6$.

Figure 5:
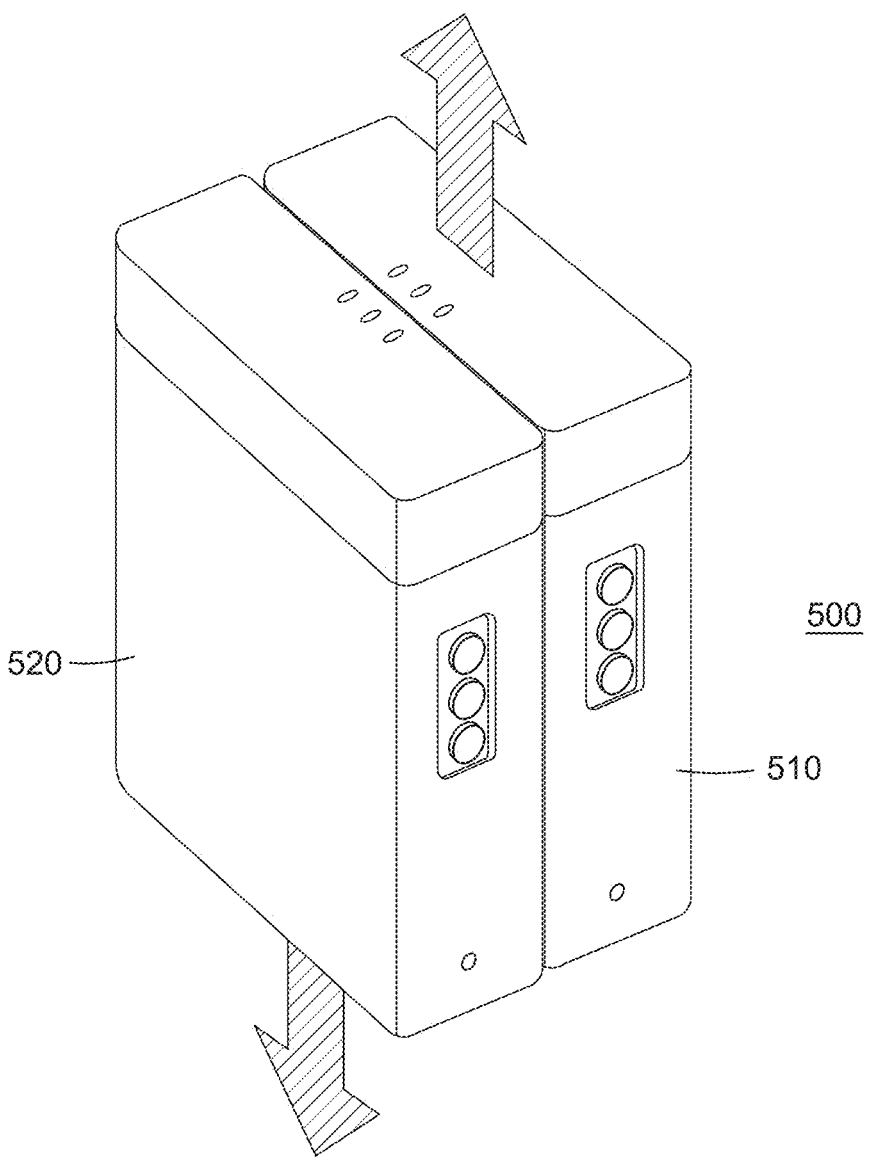
FIG. 5 shows an example modular system including an oxygen concentrator module and a compressor module.

FIG. 5 shows an example modular system 500 including an oxygen concentrator module 510 and a compressor module 520. The oxygen concentrator module 510 may house the oxygen concentrator 400 of FIG. 4 (e.g. providing 0-2 liters per minute $O_2$ or 0-20 liters per minute air at 20-30 PSI and having a 100 Wh battery with a 1-2 hour range), with the compressor module 520 housing the external compressor (e.g. providing 0-10 liters per minute air at 20-30 PSI and having a 100 Wh battery with a 2-3 hour range). As depicted by the large arrows at the top and bottom of the modular system 500, the oxygen concentrator module 510 and compressor module 520 may be detachably attached to form a single unit. For example, a user may slide the two modules 510, 520 together in the direction of the arrows to cause them to lock together as a unit with the external compressor fluid port 472 of the oxygen concentrator module 510 fluidly coupled to a compressed gas output of the compressor module 520 and with the external compressor signal port 474 of the oxygen concentrator module 510 electrically coupled to a signal input port of the compressor module 520. Sliding the two modules 510, 520 in the opposite direction may unlock and separate the modules 510, 520, allowing them to be used separately. In this way, the oxygen concentrator module 510 may be used by patients only requiring oxygen therapy, the compressor module 520 may be used by patients only requiring mechanical ventilation, and the two units combined may be used by people requiring both oxygen and mechanical ventilation. It is further contemplated that the top of the oxygen concentrator module 510 or the top of the compressor module 520 (or the combined surface formed by the tops of both the oxygen concentrator module 510 and the compressor module 520) may serve as a cradle for docking the ventilator 200. Likewise, the bottom of the oxygen concentrator module 510 or the bottom of the compressor module 520 (or the combined surface formed by the bottoms of both the oxygen concentrator module 510 and the compressor module 520) may serve as an attachment for a supplementary battery pack.

Figure 6:
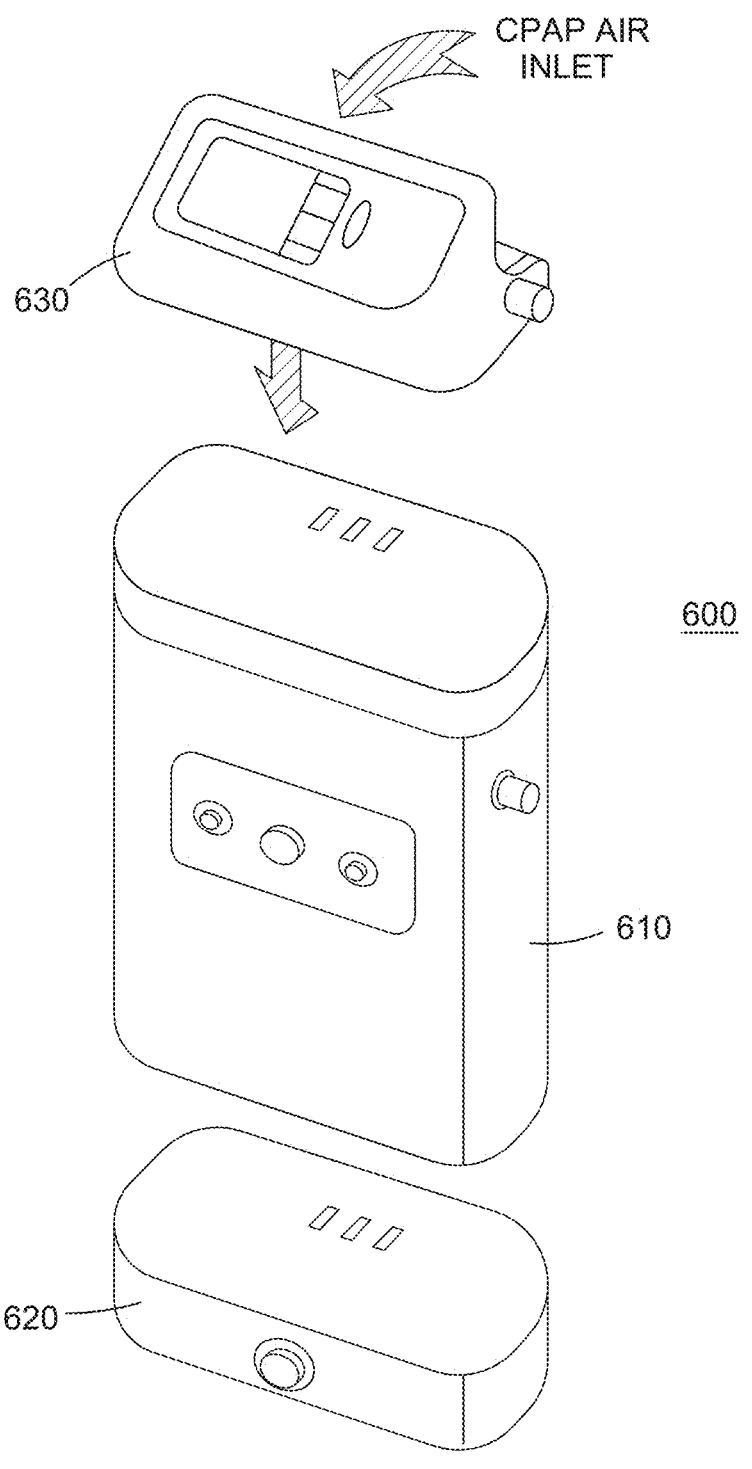
FIG. 6 shows another example modular system including an oxygen concentrator module.

FIG. 6 shows another example modular system 600 including an oxygen concentrator module 610. The oxygen concentrator module 610 may house the oxygen concentrator 100 of FIG. 1 or the oxygen concentrator module 400 of FIG. 4. As shown, the modular system 600 may have further modularity in the option to attach a supplementary hot-swappable battery pack 620 and/or a Continuous Positive Airway Pressure (CPAP) module 630 (e.g. with a 22 mm ISO Taper connector for CPAP use) to the oxygen concentrator module 610. For example, the top of the oxygen concentrator 610 may serve as a cradle for attaching the CPAP module 630 and may include a latch release and electrical contacts. Likewise, the bottom of the oxygen concentrator 610 may serve as a cradle for attaching the battery pack 620 and may include a latch release and electrical contacts. The oxygen concentrator module 610 may further include a DISS or Quick Connect and a user interface including, for example, an ON/OFF button, a battery power indicator, and a wireless ventilator connection for the ventilator 200. Such modularity may be in place of or in addition to the attachment to an external compressor module 520 as described in relation to the modular system 500 of FIG. 5.

In the above examples of the oxygen concentrator 100, 400, 510, 610, selective control of the rate of flow into the product tank 130, 430 and the oxygen concentration of the resulting product gas is achieved by means of a bypass flow path 170, 470 that bypasses the sieve beds 120, 420 of the oxygen concentrator 100, 400, 510, 610. However, the present disclosure is not intended to be so limited. For example, the controller 140, 440 may intentionally "mess up" the timing of the valves of an otherwise conventionally structured oxygen concentrator. In general, the timing of the valves of an oxygen concentrator is titrated to produce the most efficient extraction of oxygen in the sieve beds. By controlling the compressor 110, 410 and/or valve unit 150, 450 to modify the timing of the sieve bed cycles, the controller 140, 440 can intentionally prevent the oxygen and nitrogen from having enough time to separate completely in the sieve beds 120, 420. As a result, the product tank 130, 430 may be filled with a product gas having a reduced oxygen concentration and may potentially allow for higher flow rates of the product gas to the downstream ventilator 200. The controller 140, 440 may, for example, reference a lookup table of sub-optimal compressor outputs and valve control timings that do not achieve the most efficient separation of oxygen and nitrogen in the sieve beds 120, 420. Using such a lookup table, the controller 140, 440 may generate a control signal in response to a command issued by the ventilator 200 to meet the changing needs of the patient 13 in real time. In this case, the bypass flow path 170, 470 and valve $V_6$ may be omitted.

Figure 7:
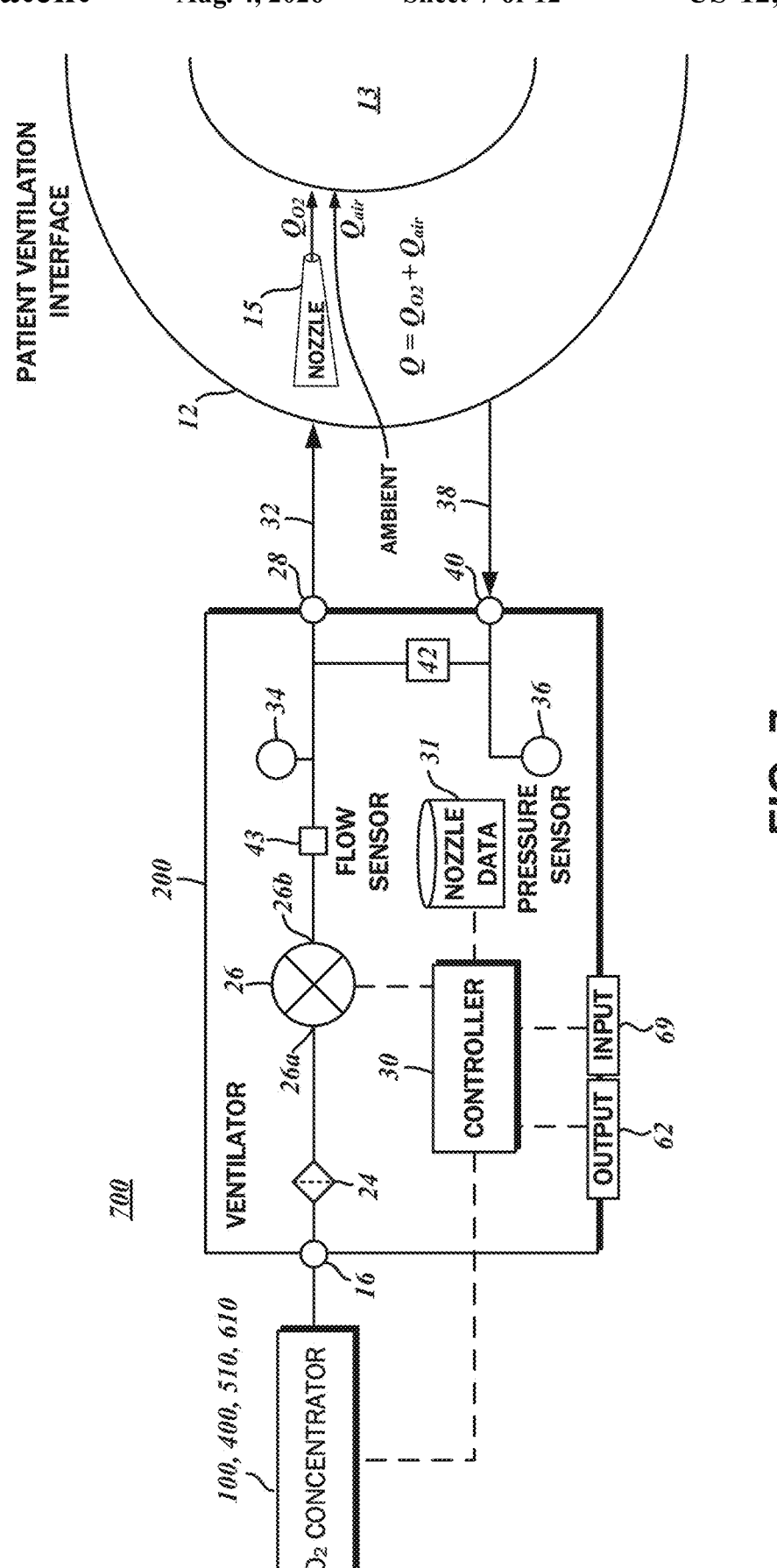
FIG. 7 shows an example ventilation system according to an embodiment of the present disclosure.

FIG. 7 shows an example ventilation system 700 according to an embodiment of the present disclosure. As shown, the ventilation system 700 may include the ventilator 200 and patient ventilation interface 12 placed in flow communication with the patient 13 as depicted in FIGS. 1 and 4, along with any of the oxygen concentrator 100, 400, 510, 610 as described in relation to FIGS. 1, 4, 5, and 6, respectively. The ventilator 200 may be arranged to deliver high oxygen content gas produced by the oxygen concentrator 100, 400, 510, 610 to the patient 13 via the patient ventilation interface 12. The patient ventilation interface 12 may include such devices as a full-face mask or a nasal mask that can be placed in direct gas flow communication with the upper respiratory tract of the patient 13, i.e., the nasal cavity and/or the oral cavity. The patient ventilation interface 12 may feature, in addition to one or more nozzles 15 for delivering the high oxygen content gas to the patient 13, one or more apertures for the entrainment of additional ambient air for delivery to the patient 13. Examples of patient ventilation interfaces 12 having nozzles 15 and entrainment apertures usable with the present disclosed subject matter can be found, for example, in U.S. Patent Application Pub. No. 2019/0099570, entitled "PATIENT INTERFACE WITH INTEGRATED JET PUMP," the entire disclosure of which is hereby incorporated by reference, and may include, for example, the Engage, Inspire, and Universal Circuit™ Connector (UCC) patient interfaces of the Life2000® Ventilation System by Breathe Technologies, Inc. As such, at any given moment, a total flow (e.g. volume flow) $Q_T$ of gas and entrained air delivered by the ventilator 200 to the patient 13 may be defined as a sum of a nozzle flow $Q_N$ of gas expelled by one or more nozzles 15 of the patient ventilation interface 12 and an entrainment flow $Q_E$ of ambient air entrained by the one or more nozzles 15. That is, the total flow $Q_T$ may be defined as $Q_T=Q_N+Q_E$. In the case of the Life2000®

Ventilation System, the flow $Q_N$ may be 5-40 L/min, which may be maintained for a duration of up to 3.0 seconds, for example.

Depending on various factors including, for example, the prescription of the patient 13, the patient's activity level, user-adjustable settings, and the state of the patient's breathing at a given moment, the entrainment flow $Q_E$ (and consequently the total flow $Q_T$) may vary, causing the patient's fraction of inspired oxygen % $FiO_2$ to vary as a greater or lesser amount of ambient air is delivered in proportion to the high oxygen content gas expelled by the one or more nozzles 15. By measuring the flow $Q_N$ of gas expelled by the one or more nozzles 15 and the pressure in the patient ventilation interface 12, the ventilator 200 may calculate or estimate the total flow $Q_T$. The ventilator 200 may instruct the oxygen concentrator 100, 400, 510, 610 to produce a specific flow of gas having a specific oxygen concentration according to the estimated or calculated total flow $Q_T$. The ventilator 200 may then provide such high oxygen content gas to the patient 13 via the patient ventilation interface 12 such that, taking into account the entrainment of additional ambient air in the patient ventilation interface 12, the patient 13 is provided with a desired degree of assistance to the patient's work of breathing and a target % $FiO_2$.

The ventilator 200 may include a first inlet port 16 through which the high oxygen content gas is provided to the ventilator 200 by the oxygen concentrator 100, 400, 510, 610. The first inlet port 16 may be in communication with an inlet filter 24 that removes particulates and other contaminants from the breathing gas that is ultimately delivered to the patient. The pressure of the high oxygen content gas originating from the oxygen concentrator 100, 400, 510, 610 may be regulated by a valve 26 having a valve inlet port 26*a* in gas flow communication with the inlet filter 24 and a valve outlet port 26*b* that is in gas flow communication with an outlet port 28 of the ventilator 14. The state of the valve 26 may be selectively adjusted to port a desired volume/pressure of gas from the oxygen concentrator 100, 400, 510, 610 to the patient 13. The actuation of the valve 26 may be governed by a controller 30 that implements various methods contemplated by the present disclosure, as will be described in further detail below.

The flow of breathing gas that is ported through the valve 26 may be passed through the outlet port 28 to a gas delivery conduit 32 that is coupled to the aforementioned patient ventilation interface 12. The gas delivery conduit 32 is may be, for example, a plastic tube having a predetermined inner diameter such as 22 mm or smaller. A pressure difference may be generated between the patient ventilation interface 12 and the output of the valve 26, i.e., the valve outlet 26*a*, depending on the state of respiration of the patient 13.

In order to ascertain such pressure differentials, the ventilation system 700 may include dual pressure sensors, including a valve pressure sensor 34 and a patient interface pressure sensor 36. The valve pressure sensor 34 may be disposed within the ventilator 200 and may monitor the pressure at the valve outlet port 26*b*. The patient interface pressure sensor 36 may also be physically disposed within the ventilator 200 but in direct gas flow communication with the patient ventilation interface 12 over a pressure sensor line 38 that is connected to a sensor inlet port 40 of the ventilator 200. When the ventilator 200 is operating, gas pressure within the pressure sensor line 38 as well as the gas conduit 32 may be connected to deliver a purge flow to clear the pressure sensor line 38. This can be done through a purge solenoid 42 connected to both. The purge can be continuous or intermittent according to the patient's breathing phase or pressure difference between the valve pressure and the patient interface pressure.

In addition to measuring pressure differentials at the patient ventilation interface 12 and the valve output 26b, flow measurements of the breathing gas actually output from the valve 26 may be utilized. To this end, the ventilator 200 may include a flow sensor 43 that is in-line with the valve 12 and the outlet port 28.

The ventilator 200 may measure the pressure in the patient ventilation interface 12 and the flow of gas expelled by the one or more nozzles 15 of the patient ventilation interface 12. For example, the controller 30 may communicate with one or both of a valve pressure sensor 34 and a patient interface pressure sensor 36 to measure the pressure and may communicate with the flow sensor 43 to measure the flow. Based on the measured pressure and flow, the controller 30 may then estimate or calculate the total flow $Q_T$ and/or various other parameters as described in more detail below. To this end, the ventilator 200 may further include a nozzle data storage 31 that may store one or more constants in association with each of a plurality of nozzle geometries. During use, the controller 30 may calculate the total flow $Q_T$ based on the measured flow, the measured pressure, and the one or more constants stored in association with the nozzle geometry of the one or more nozzles 15. Based on the calculated total flow $Q_T$, the controller 30 may further calculate the patient's % $FiO_2$. The controller 30 may continually calculate the total flow $Q_T$ and/or % $FiO_2$ of the patient 13 in real time as the user's activity level and breathing changes and as user-adjustable settings of the ventilator 200 are modified (e.g. using an input 69 such as a touch screen or buttons and an output 62 such as a display).

Based on the calculated total flow $Q_T$ and/or the patient's % $FiO_2$, the controller 30 may instruct the oxygen concentrator 100, 400, 510, 610, for example, by causing a signal (e.g. a radio frequency wireless signal) to be transmitted from the ventilator 200 to the oxygen concentrator 100, 400, 510, 610. Upon receipt of the signal from the ventilator 200, the oxygen concentrator 100, 400, 510, 610 may adjust the pressure, flow, and/or oxygen concentration of the high oxygen content gas that it produces in order to meet the changing needs of the patient in real time. Such adjustments may be made within the oxygen concentrator 100, 400, 510, 610 as described above in relation to FIGS. 1 and 4. In this way, the ventilator 200 may control the oxygen concentrator 100, 400, 510, 610 according to a master/slave arrangement with the ventilator 200 functioning as master and the oxygen concentrator 100, 400, 510, 610 functioning as slave.

Figure 8:
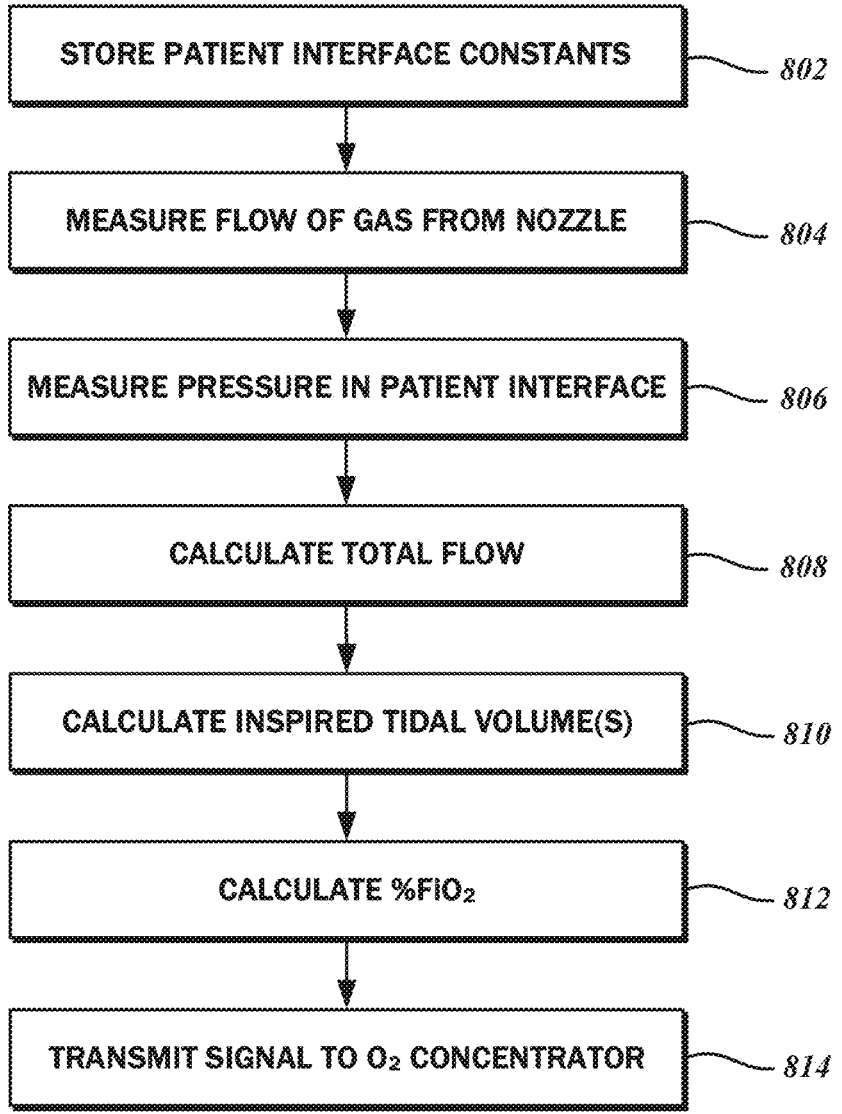
FIG. 8 shows an example operational flow that may be performed, in whole or in part, by the ventilator.

FIG. 8 shows an example operational flow that may be performed, in whole or in part, by the ventilator 200 in accordance with an embodiment of the disclosed subject matter. The operational flow of FIG. 8 may be used to calculate the total flow $Q_T$ from the measured flow $Q_N$ (nozzle flow) of gas expelled by one or more nozzles 15 and the measured pressure $P_{aw}$ (airway pressure) in the patient ventilation interface 12. Equivalently, with the flow $Q_N$ of gas expelled by one or more nozzles 15 being known, the operational flow of FIG. 8 may be used to calculate the entrainment flow $Q_E = Q_T - Q_N$ generated by the flow $Q_N$ through the nozzle(s) 15, as well as various other values derivable therefrom.

In general, entrainment is affected by the pressure downstream of the nozzle, which, in the case of the nozzle(s) 15 of a patient ventilation interface 12 such as that of the Life2000® system, may be regarded as the measured pressure $P_{aw}$. When the pressure $P_{aw}$ reaches the stagnation pressure $P_S$, the flow $Q_N$ through the nozzle(s) 15 equals 0 to due to back pressure in the patient's airways and lungs. The stagnation pressure $P_S$ may be used to calculate the total flow $Q_T$ as a function of $Q_N$ and $P_{aw}$ according to the following equation:

$$Q_T(Q_N, P_{aw}) = \left(1 - \frac{P_{aw}}{P_S(Q_N)}\right) * Q_N * c,$$

where the stagnation pressure $P_S$ is a function of the flow $Q_N$ of expelled gas and may be calculated as the quadratic $$P_S(Q_N) = a * Q_N^2 + b * Q_N$$

and a, b, and c are constants that depend on the specific nozzle geometry. The constants a, b, and c may be determined in advance for each nozzle geometry by finding the stagnation pressure that a given flow will generate. In the case of the UCC patient interface of the Life2000® system, a=0.0191 and b=0.3828 to yield the calculated relationship shown in FIG. 9 between the pressure $P_{aw}$ at stagnation pressure and the nozzle pressure $Q_N$, i.e. the stagnation pressure $P_S$ as a function of nozzle flow $Q_N$, or $P_S(Q_N)$. For the UCC patient interface, c=8, yielding the calculated relationship shown in FIG. 10 between the total pressure $Q_T$ and the pressure $P_{aw}$ for each of a plurality of nozzle flows $Q_N$ (5, 10, 20, 30, and 40 L/min).

The operational flow of FIG. 8 may begin with a step 802 of storing one or more constants in association with each of a plurality of nozzle geometries. For example, the above constants a, b, and c may be stored for each of a plurality of nozzle geometries, such as for the Engage, Inspire, and UCC patient interfaces of the Life2000® system. These constants may be stored, for example, in the nozzle data storage 31 shown in FIG. 7. Alternatively, the constants may be stored in the patient ventilation interfaces 12 themselves, such as in a memory (e.g. EEPROM) disposed in a harness thereof, such that each patient ventilation interface 12 may store the constants a, b, and c associated with its own particular nozzle geometry. This may allow individual nozzles to be calibrated separately from the ventilator 200 to account for manufacturing differences between nozzles.

During the treatment of a patient 13 using the ventilation system 700, the operational flow of FIG. 8 may proceed with a step 804 of measuring a flow $Q_N$ of gas expelled from one or more nozzles 15 of the patient ventilation interface 12 and a step 806 of measuring a pressure $P_{aw}$ in the patient ventilation interface 12. Measuring the pressure $P_{aw}$ may include communication between the controller 30 and both the valve pressure sensor 34 and the patient interface pressure sensor 36. For example, the measured pressure $P_{aw}$ may be defined as the difference between the pressure in the patient ventilation interface 12 as measured by the patient interface pressure sensor 36 and the pressure at the valve outlet port 26b as measured by the valve pressure sensor 34. With the measured flow $Q_N$ and the measured pressure $P_{aw}$ having been acquired, the operational flow may continue with a step 808 of calculating the total flow $Q_T$ of gas and entrained air delivered by the ventilator 200 to the patient 13. For example, the controller 30 may calculate the total flow $Q_T$ based on the measured flow $Q_N$ and the measured pressure $P_{aw}$ along with the stored constants a, b, and c using the above equations, e.g., by using the constants a and b and the measured flow $Q_N$ to calculate the stagnation pressure $P_S$ and then using the measured flow $Q_N$, the measured pressure $P_{aw}$, the stagnation pressure $P_S$, and the constant c to calculate the total flow $Q_T$. In calculating the total flow $Q_T$, the controller 30 may read the constants a, b, and c from the nozzle data storage 31 or, in a case where the constants are stored in a memory of the patient ventilation interface 12, the controller 30 may read the constants a, b, and c from the external memory upon connection of the patient ventilation interface 12 to the ventilator 200 (e.g. via smart connector that downloads the constants to the ventilator 200).

In a step 810, any of various values derivable from the total flow $Q_T$ may be calculated, such as one or more inspired tidal volumes. For example, a total inspired tidal volume $TotV_t$ may be calculated as an integral of the total flow $Q_T$ with respect to time, an inspired tidal volume $NozV_t$ of the gas expelled by the one or more nozzles 15 may be calculated as an integral of the measured flow $Q_N$ with respect to time, and/or an inspired tidal volume $EntV_t$ of entrained air may be calculated as an integral with respect to time of the entrained flow $Q_E=Q_T-Q_N$. In a step 812, the controller 30 may calculate the % $FiO_2$ based on the inspired tidal volume of the gas expelled by the one or more nozzles 15 and the inspired tidal volume of entrained air. For example, assuming the gas expelled by the one or more nozzles 15 is 100% oxygen, the % $FiO_2$ may be calculated as % $FiO_2=100$ $(NozV_t+0.21$ $EntV_t)/TotV_t$, where 21% is the approximate percentage of oxygen in ambient air. More generally, for an arbitrary gas expelled by the one or more nozzles 15 (for example, in a case where the oxygen concentrator 100, 400, 510, 610 is controlled to deliver a lower oxygen concentration as described above), the % $FiO_2$ may be calculated as % $FiO_2=100$ $(NozV_t+0.21$ $EntV_t)/$ $TotV_t$, where 100x is the percentage of oxygen included in the gas expelled by the one or more nozzles 15. The value X defining the oxygen concentration of the gas supplied from the expelled by the one or more nozzles 15 may be determined from the known oxygen concentration of the gas supplied from the oxygen concentrator 100, 400, 510, 610, for example, based on the current/previous setpoint issued by the controller 30 and/or a measurement of the oxygen concentration sensor 190.

Lastly, in a step 814, the controller 30 of the ventilator 200 may instruct the oxygen concentrator 100, 400, 510, 610 based on the calculated total flow $Q_T$ or % $FiO_2$, for example, by causing a signal to be transmitted from the ventilator 200 to the oxygen concentrator 100, 400, 510, 610 as described above. Upon receipt of the signal from the ventilator 200, the oxygen concentrator 100, 400, 510, 610 may adjust the pressure, flow, and/or oxygen concentration of the high oxygen content gas that it produces to produce a desired total flow $Q_T$ and/or % $FiO_2$.

In the above example, the constants a, b, and c are stored for each nozzle geometry. However, it is also contemplated that only the constant c may be stored for each nozzle geometry, with the stagnation pressure $P_S$ further being stored for a range of possible flows $Q_N$. In a case where the ventilator 200 is designed for use only with a single nozzle geometry, it may be unnecessary to store any constants at all and step 802 can be omitted. The total flow $Q_T$ can simply be calculated as a function of the measured flow $Q_N$ and the measured pressure $P_{aw}$ without modifying the above equation for different nozzle geometries.

Figure 9:
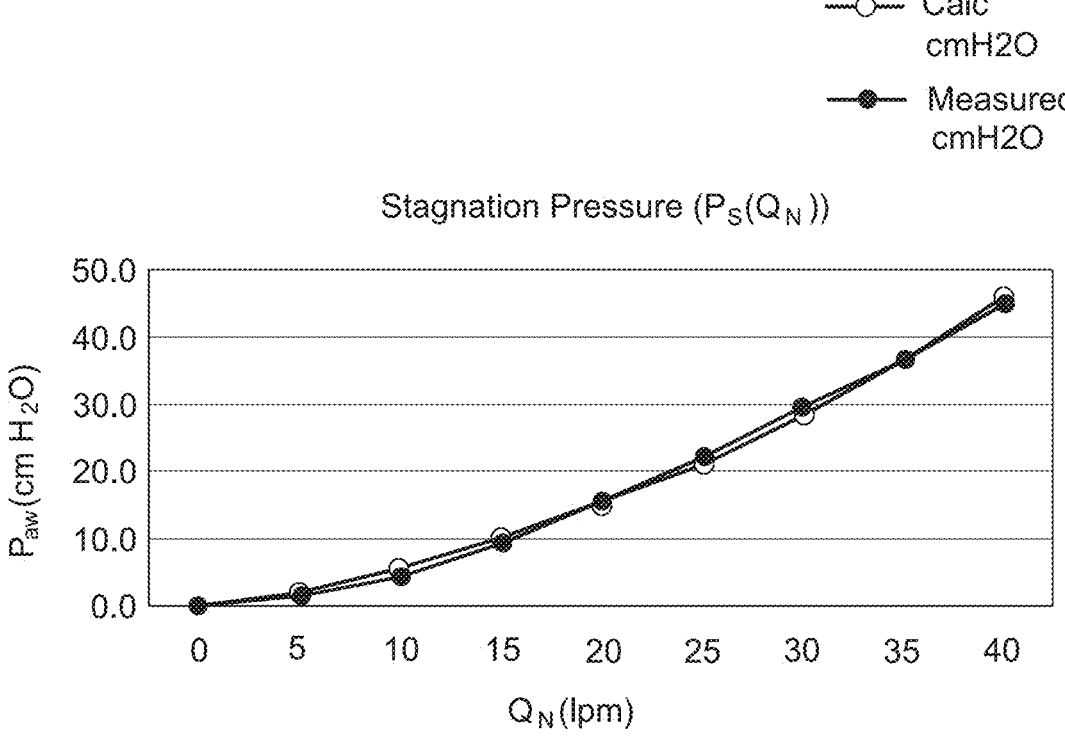
FIG. 9 shows an example of calculated and measured stagnation pressure of a nozzle at different flows.

FIG. 9 shows an example of calculated and measured stagnation pressure of a nozzle at different flows. As explained above, the calculated relationship shown in FIG. 9 was generated using the constants a=0.191 and b=0.3828 and the above equation for the stagnation pressure $P_S$. The other relationship ("Measured cmH20") shown in FIG. 9 is the experimental results of measuring the stagnation pressure $P_S$ of the UCC patient interface. As can be seen in FIG. 9, the measured relationship closely matches the calculated relationship, demonstrating that there is a quadratic relationship between stagnation pressure $P_S$ and nozzle flow $Q_N$.

Figure 10:
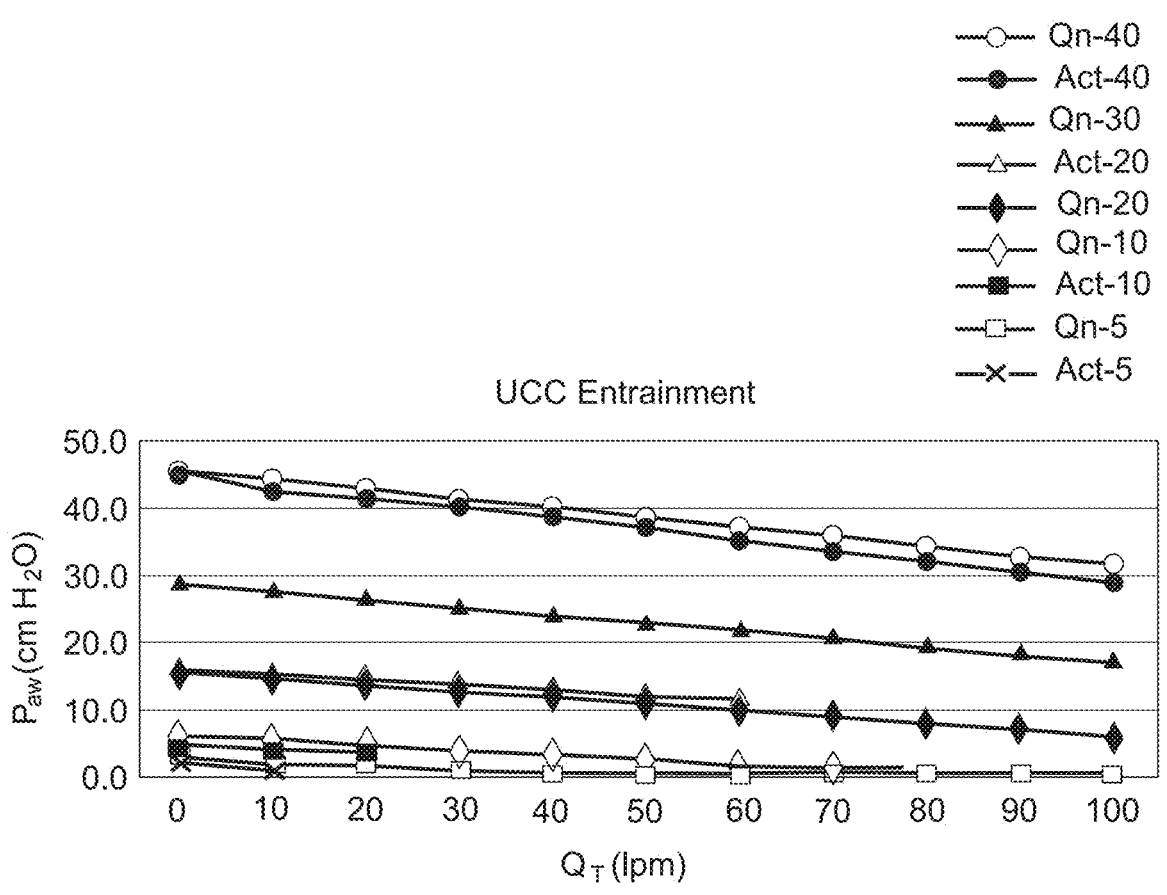
FIG. 10 shows an example of calculated and measured characteristic $P_{aw}$–$Q_T$ curves of a nozzle for different flows.

FIG. 10 shows an example of calculated and measured $P_{aw}-Q_T$ curves for a nozzle at different flows. As explained above, the calculated relationships shown in FIG. 10 were generated using the constant c=8 and the above equation for the total flow $Q_T$ as a function of airway pressure $P_{aw}$ for different nozzle flows $Q_N$. The other relationships ("Act-5," "Act-10," etc.) are the actual experimental results of measuring the relationship between the total flow $Q_T$ and the airway pressure $P_{aw}$ for 5, 10, 20, and 40 L/min nozzle flows $Q_N$. As can be seen in FIG. 10, the measured relationships closely match the calculated relationships, demonstrating that there is a linear relationship between airway pressure $P_{aw}$ and total flow $Q_T$.

Figure 11:
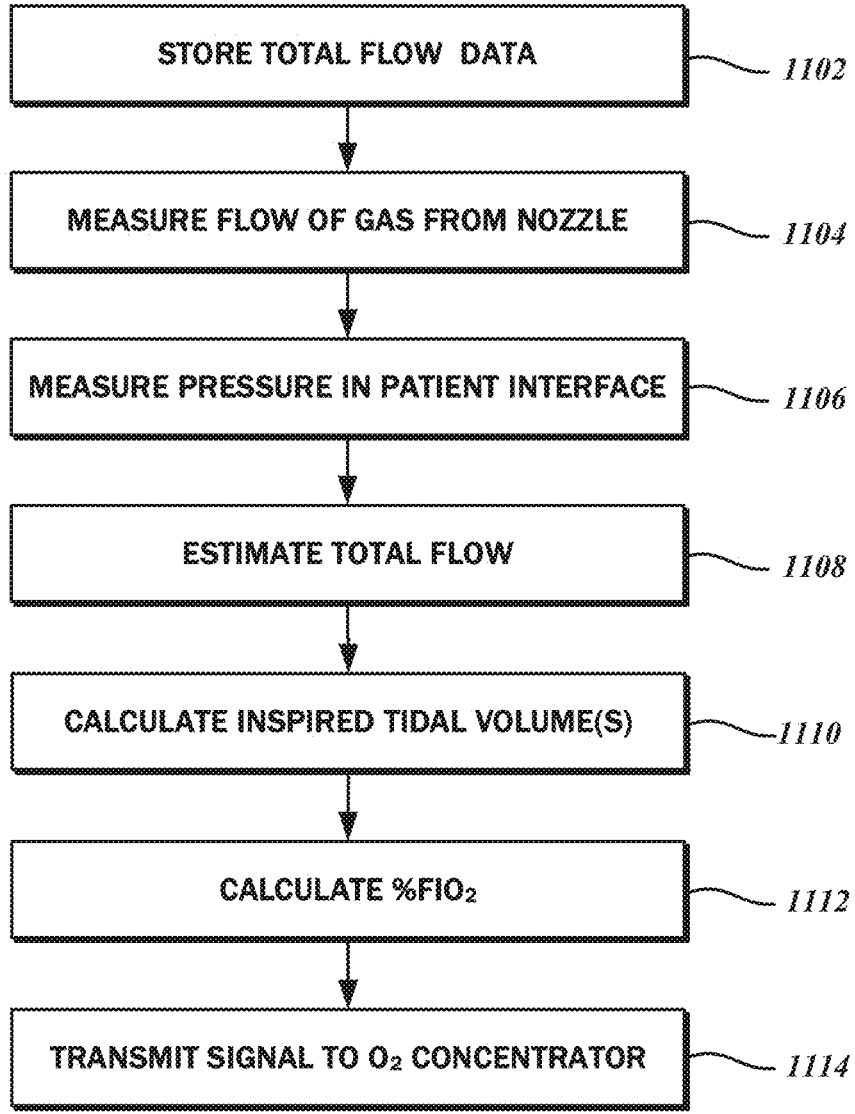
FIG. 11 shows another example operational flow that may be performed, in whole or in part, by the ventilator.

FIG. 11 shows another example operational flow that may be performed, in whole or in part, by the ventilator 200 in accordance with an embodiment of the disclosed subject matter. In the example of FIG. 11, rather than calculating the total flow $Q_T$ using the constants a, b, and c and the relationship between total flow $Q_T$ and stagnation pressure $P_S$ as described above, the predetermined characteristic $P_{aw}-Q_T$ curves for a given nozzle (or plurality of nozzles) may be stored in advance and used to estimate the total flow $Q_T$ for a measured pressure $P_{aw}$ and nozzle flow $Q_N$. The operational flow may begin with a step 1102 of storing total flow data, for example, in the nozzle data storage 31 of the ventilator 200. By way of example, the total flow data may include the characteristic curves (e.g. the underlying data thereof, which may be stored in table form or as parameterized equations) of FIG. 10 for one or more nozzles. As in the case of storing the constants a, b, c, the pre-stored characteristic curves may alternatively be stored in a memory in each patient interface 12, characterizing that particular patient interface 12. With respect to a given patient interface 12, the nozzle data storage 31 or external memory may store, for each of a plurality of measurements of a flow $Q_N$ of gas expelled by the one or more nozzles 15 of the patient ventilation interface 12 (e.g. $Q_N=5$, 10, 20, 30, 40 as shown in FIG. 10), a plurality of measurements of total flow $Q_N$ in correspondence with a plurality of measurements of the pressure $P_{aw}$ in the patient ventilation interface 12.

During the treatment of a patient 13 using the ventilation system 700, the operational flow of FIG. 11 may proceed with a step 1104 of measuring a flow $Q_N$ of gas expelled from one or more nozzles 15 of the patient ventilation interface 12 and a step 1106 of measuring a pressure $P_{aw}$ in the patient ventilation interface 12 as described above. With the measured flow $Q_N$ and the measured pressure $P_{aw}$ having been acquired, the operational flow may continue with a step 1108 of estimating the total flow $Q_T$ based on a comparison of the measured pressure $P_{aw}$ to the plurality of measurements of total flow $Q_T$ stored for the measured flow $Q_N$. For example, the controller 30 may reference the nozzle data storage 31 to consult the characteristic $P_{aw}-Q_T$ curves shown in FIG. 10, find the characteristic $P_{aw}-Q_T$ curve corresponding to the measured flow $Q_N$, and read the value of the total flow $Q_T$ corresponding to the measured pressure $P_{aw}$ along that curve.

With the total flow $Q_T$ having been estimated as described above, the operational flow of FIG. 11 may proceed with a step 1110 of calculating one or more inspired tidal volume(s)

or any of various other values derivable from the total flow $Q_T$, a step 1112 of calculating the % $FiO_2$ of the patient 13, and a step 1114 of transmitting a signal to the oxygen concentrator 100, all of which can be performed in the same way as the steps 810, 812, and 814 of the operational flow of FIG. 8. The only difference is that, in the case of FIG. 10, the total flow $Q_T$ was estimated using pre-stored characteristic curves rather than being calculated using the measured pressure $P_{aw}$, the measured flow $Q_N$, and one or more constants characterizing the patient interface 12. Upon receipt of the signal from the ventilator 14, the oxygen concentrator 18 may adjust the pressure, flow, and/or oxygen concentration of the high oxygen content gas that it produces to produce a desired total flow $Q_T$ and/or % $FiO_2$.

Figure 12:
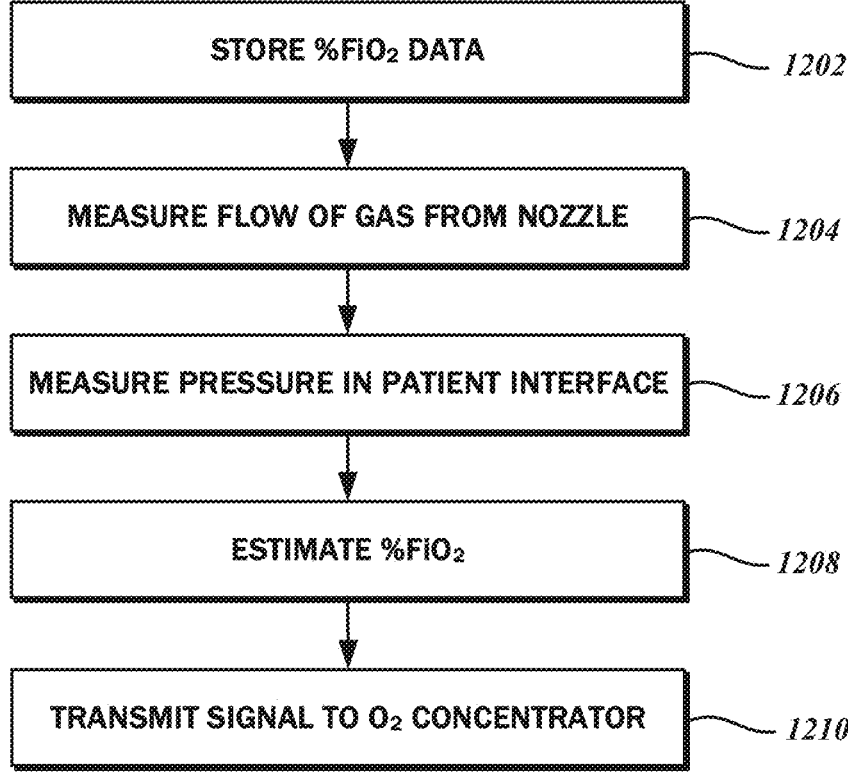
FIG. 12 shows another example operational flow that may be performed, in whole or in part, by the ventilator.

FIG. 12 shows another example operational flow that may be performed, in whole or in part, by the ventilator 200 in accordance with an embodiment of the disclosed subject matter. In the example of FIG. 12, rather than estimating the total flow $Q_T$ as a precursor to calculating the % $FiO_2$ of the patient, % $FiO_2$ data of each nozzle may be stored in advance and used to estimate the % $FiO_2$ for a measured pressure $P_{aw}$ and nozzle flow $Q_N$. The operational flow may begin with a step 1202 of storing % $FiO_2$ data, for example, in the nozzle data storage 31 of the ventilator 200. The % $FiO_2$ data may include characteristic curves (e.g. the underlying data thereof, which may be stored in table form or as parameterized equations) for one or more nozzles. As in the case of storing the constants a, b, c, the pre-stored characteristic curves may alternatively be stored in a memory in each patient interface 12, characterizing that particular patient interface 12. With respect to a given patient interface 12, the nozzle data storage 31 or external memory may store, for each of a plurality of measurements of a flow $Q_N$ of gas expelled by the one or more nozzles 15 of the patient ventilation interface 12 (e.g. $Q_N$=5, 10, 20, 30, 40 as shown in FIG. 10), a plurality of measurements of % $FiO_2$ in correspondence with a plurality of measurements of the pressure $P_{aw}$ in the patient ventilation interface 12. Such characteristic $P_{aw}$-% $FiO_2$ curves may be obtained experimentally by measuring % $FiO_2$ in a laboratory at a variety of pressures $P_{aw}$ and nozzle flows $Q_N$ or may be derived from the total flow data described above with respect to the operational flow of FIG. 11.

During the treatment of a patient 13 using the ventilation system 700, the operational flow of FIG. 11 may proceed with a step 1204 of measuring a flow $Q_N$ of gas expelled from one or more nozzles 15 of the patient ventilation interface 12 and a step 1206 of measuring a pressure $P_{aw}$ in the patient ventilation interface 12 as described above. With the measured flow $Q_N$ and the measured pressure $P_{aw}$ having been acquired, the operational flow may continue with a step 1208 of estimating the patient's $FiO_2$ based on a comparison of the measured pressure $P_{aw}$ to the plurality of measurements of $FiO_2$ stored for the measured flow $Q_N$. For example, the controller 30 may reference the nozzle data storage 31 to consult the % $FiO_2$ data for the particular one or more nozzles 15, find the characteristic $P_{aw}$-% $FiO_2$ curve corresponding to the measured flow $Q_N$, and read the value of the % $FiO_2$ corresponding to the measured pressure $P_{aw}$ along that curve. With the patient's % $FiO_2$ having been estimated as described above, the operational flow of FIG. 12 may proceed with a step 1210 of transmitting a signal to the oxygen concentrator 100, which can be performed in the same way as step 814 of FIG. 8 or step 1114 of FIG. 11. The only difference is that, in the case of FIG. 12, the % $FiO_2$ was estimated directly using pre-stored characteristic curves rather than being calculated from the total flow $Q_T$. Upon receipt of the signal from the ventilator 14, the oxygen concentrator 18 may adjust the pressure, flow, and/or oxygen concentration of the high oxygen content gas that it produces to produce a desired entrainment ratio and/or % $FiO_2$.

The above example operational flows of FIGS. 8, 11, and 12 the total flow $Q_T$ and or patient's % $FiO_2$ is calculated or estimated and used to characterize the needs of the patient 13 in a given moment for the purpose of controlling an oxygen concentrator 100. However, the disclosed subject matter is not intended to be limited to these specific parameters. For example, various derived or otherwise related parameters may be used instead, such as the entrainment flow $Q_E$, an entrainment ratio $\eta=(Q_T-Q_N)/Q_N$, or the tidal volume $TotV_t$, $NozV_t$, or $EntV_t$. Using the disclosed subject matter, any and all such values may be calculated and/or estimated based on the measured patient airway pressure $P_{aw}$ and the nozzle flow $Q_N$.

The controller 140, 440 of the oxygen concentrator 100, 400 and/or the controller 30 of the ventilator 200 and their respective functionality may be implemented with a programmable integrated circuit device such as a microcontroller or control processor. Broadly, the device may receive certain inputs, and based upon those inputs, may generate certain outputs. The specific operations that are performed on the inputs may be programmed as instructions that are executed by the control processor. In this regard, the device may include an arithmetic/logic unit (ALU), various registers, and input/output ports. External memory such as EEPROM (electrically erasable/programmable read only memory) may be connected to the device for permanent storage and retrieval of program instructions, and there may also be an internal random access memory (RAM). Computer programs for implementing any of the disclosed functionality of the controller 140, 440 and/or controller 30 may reside on such non-transitory program storage media, as well as on removable non-transitory program storage media such as a semiconductor memory (e.g. IC card), for example, in the case of providing an update to an existing device. Examples of program instructions stored on a program storage medium or computer-readable medium may include, in addition to code executable by a processor, state information for execution by programmable circuitry such as a field-programmable gate arrays (FPGA) or programmable logic device (PLD).

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for estimating a fraction of inspired oxygen % $FiO_2$ of a patient receiving ventilatory support from a ventilator, the method comprising:

storing, for each of a plurality of measurements of a flow rate of gas expelled by one or more nozzles of a patient ventilation interface connected to the ventilator, a plurality of measurements of % $FiO_2$ in correspondence with a plurality of measurements of pressure in the patient ventilation interface, the patient ventilation interface including, in addition to the one or more nozzles, one or more apertures for the entrainment of additional ambient air for delivery to the patient;

measuring a flow rate of gas expelled by the one or more nozzles;

measuring a pressure in the patient ventilation interface; and estimating the % $FiO_2$ of the patient based on a comparison of the measured pressure to the plurality of measurements of % $FiO_2$ stored for the measured flow rate.

2. The method of claim 1, further comprising transmitting a signal to an oxygen concentrator based on the estimated % $FiO_2$.

3. The method of claim 1, further comprising:

storing one or more constants in association with each of a plurality of nozzle geometries, wherein each of the one or more nozzles has a nozzle geometry corresponding to one of the plurality of nozzle geometries, wherein said estimating the % $FiO_2$ of the patient is further based on the one or more constants stored in association with the nozzle geometry of the one or more nozzles.

4. The method of claim 3, wherein, for each of the plurality of nozzle geometries, the associated one or more constants are stored in a memory disposed in a patient ventilation interface with a nozzle having that nozzle geometry, and said estimating the % $FiO_2$ of the patient includes reading the one or more constants stored in the patient ventilation interface connected to the ventilator.

5. A non-transitory program storage medium on which are stored instructions executable by a processor or programmable circuit to perform operations for controlling an oxygen concentrator connected to a ventilator based on a fraction of inspired oxygen % $FiO_2$ of a patient receiving ventilatory support from the ventilator, the operations comprising:

storing, for each of a plurality of measurements of a flow rate of gas expelled by one or more nozzles of a patient ventilation interface connected to the ventilator, a plurality of measurements of % $FiO_2$ in correspondence with a plurality of measurements of pressure in the patient ventilation interface, the patient ventilation interface including, in addition to the one or more nozzles, one or more apertures for the entrainment of additional ambient air for delivery to the patient;

measuring a flow rate of gas expelled by the one or more nozzles;

measuring a pressure in the patient ventilation interface; and estimating the % $FiO_2$ of the patient based on a comparison of the measured pressure to the plurality of measurements of % $FiO_2$ stored for the measured flow rate.

6. A ventilator comprising:

the non-transitory program storage medium of claim 5;

a processor or programmable circuit for executing the instructions;

a flow sensor; and a pressure sensor, wherein said measuring the flow rate includes communicating with the flow sensor, and said measuring the pressure includes communicating with the pressure sensor.

7. A ventilation system comprising:

the ventilator of claim 6; and an oxygen concentrator connected to the ventilator, wherein the operations further comprise transmitting a signal from the ventilator to the oxygen concentrator based on the estimated % $FiO_2$.

8. The ventilation system of claim 7, wherein the oxygen concentrator includes a controller operable to generate a control signal in response to the signal transmitted from the ventilator, the control signal generated by the controller selectively allowing flow of pressurized ambient air into a product tank of the oxygen concentrator.

9. The ventilation system of claim 8, wherein the control signal generated by the controller operates a valve unit of the oxygen concentrator to maintain a preset oxygen concentration in the product tank according to the signal transmitted from the ventilator.

10. The ventilation system of claim 9, wherein the control signal generated by the controller operates the valve unit to allow the flow of pressurized ambient air to bypass one or more sieve beds of the oxygen concentrator.

11. The ventilation system of claim 8, wherein the control signal generated by the controller operates a compressor of the oxygen concentrator to maintain a preset oxygen concentration in the product tank according to the signal transmitted from the ventilator.

12. The ventilation system of claim 8, wherein the control signal generated by the controller operates a compressor external to the oxygen concentrator to maintain a preset oxygen concentration in the product tank according to the signal transmitted from the ventilator.

13. A ventilation system comprising:

a ventilator;

a patient ventilation interface connectable to the ventilator and including one or more nozzles for expelling a flow of gas and one or more apertures for entrainment of additional ambient air for delivery to a patient;

a data storage storing, for each of a plurality of measurements of a flow rate of gas expelled by the one or more nozzles, a plurality of measurements of % $FiO_2$ in correspondence with a plurality of measurements of pressure in the patient ventilation interface;

a flow sensor operable to measure a flow rate of gas expelled by the one or more nozzles;

a pressure sensor operable to measure a pressure in the patient ventilation interface; and a controller operable to estimate the % $FiO_2$ of the patient based on a comparison of the measured pressure to the plurality of measurements of % $FiO_2$ stored for the measured flow rate.

14. The ventilation system of claim 13, further comprising:

an oxygen concentrator connected to the ventilator, wherein the ventilator is operable to transmit a signal to the oxygen concentrator based on the estimated % $FiO_2$.

15. The ventilation system of claim 14, wherein the oxygen concentrator is operable to generate a control signal in response to the signal transmitted from the ventilator, the control signal generated by the oxygen concentrator selectively allowing flow of pressurized ambient air into a product tank of the oxygen concentrator.

16. The ventilation system of claim 15, wherein the control signal generated by the oxygen concentrator operates a valve unit of the oxygen concentrator to maintain a preset oxygen concentration in the product tank according to the signal transmitted from the ventilator.

17. The ventilation system of claim 16, wherein the control signal generated by the oxygen concentrator operates the valve unit to allow the flow of pressurized ambient air to bypass one or more sieve beds of the oxygen concentrator.

18. The ventilation system of claim 15, wherein the control signal generated by the oxygen concentrator operates a compressor of the oxygen concentrator to maintain a preset oxygen concentration in the product tank according to the signal transmitted from the ventilator.

19. The ventilation system of claim 15, wherein the control signal generated by the oxygen concentrator operates a compressor external to the oxygen concentrator to maintain a preset oxygen concentration in the product tank according to the signal transmitted from the ventilator.

20. The ventilation system of claim 13, wherein the controller is operable to estimate the % $FiO_2$ of the patient further based on one or more constants stored in association with a nozzle geometry of the one or more nozzles.

* * * * *